(12) United States Patent
Curran

(10) Patent No.: US 12,137,988 B2
(45) Date of Patent: Nov. 12, 2024

(54) SYSTEM AND METHOD FOR NOISE TOLERANT CARDIAC LOCALIZATION, NAVIGATION AND MAPPING

(71) Applicant: ST. JUDE MEDICAL, CARDIOLOGY DIVISION, INC., St. Paul, MN (US)

(72) Inventor: Timothy G. Curran, St. Paul, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 410 days.

(21) Appl. No.: 17/619,990

(22) PCT Filed: Jul. 15, 2020

(86) PCT No.: PCT/US2020/042177
§ 371 (c)(1),
(2) Date: Dec. 16, 2021

(87) PCT Pub. No.: WO2021/011685
PCT Pub. Date: Jan. 21, 2021

(65) Prior Publication Data
US 2022/0296309 A1    Sep. 22, 2022

Related U.S. Application Data

(60) Provisional application No. 62/875,557, filed on Jul. 18, 2019.

(51) Int. Cl.
*A61B 34/20* (2016.01)
*A61B 5/00* (2006.01)
(Continued)

(52) U.S. Cl.
CPC .............. *A61B 34/20* (2016.02); *A61B 5/062* (2013.01); *A61B 5/063* (2013.01); *A61B 5/068* (2013.01);
(Continued)

(58) Field of Classification Search
CPC ...... A61B 2034/102; A61B 2034/2051; A61B 34/10; A61B 34/20; A61B 5/062;
(Continued)

(56) References Cited

U.S. PATENT DOCUMENTS

2009/0203992 A1   8/2009   Govari et al.
2012/0035605 A1   2/2012   Tegg et al.
(Continued)

FOREIGN PATENT DOCUMENTS

CN        1582385 A      2/2005
CN      101622784 A      1/2010
(Continued)

OTHER PUBLICATIONS

PCT/US2020/042177, "International Search Report and Written Opinion", Oct. 30, 2020, 17 pages.
(Continued)

*Primary Examiner* — Mark D Remaly
(74) *Attorney, Agent, or Firm* — Billion & Armitage

(57) ABSTRACT

The present disclosure is directed to interleaving electrical noise generating operations with impedance measurements in a medical localization system. The systems and methods continuously and simultaneously provide unique frequency drive signals, which are harmonics of a common base frequency, across electrode patches to generate an electrical field. Response signals electrodes in the electric field are measured and synchronously demodulated. A demodulated data stream is then filtered (e.g., decimated) to generate impedance-based values proportional to the location of the
(Continued)

electrode for each unique frequency. The demodulated data stream into the filter is paused to allow operation of an electrical noise generating device such a magnetic field-based localization system. More specifically, the data stream is paused for a time period equal to an integer multiple of a base period of the common base frequency. This allows resuming filtering of the demodulated data stream free of any frequency discontinuity.

20 Claims, 13 Drawing Sheets

(51) Int. Cl.
*A61B 5/06* (2006.01)
*A61B 34/10* (2016.01)

(52) U.S. Cl.
CPC .............. *A61B 5/742* (2013.01); *A61B 34/10* (2016.02); *A61B 2034/102* (2016.02); *A61B 2034/2051* (2016.02)

(58) Field of Classification Search
CPC ....... A61B 5/063; A61B 5/068; A61B 5/6852; A61B 5/742
See application file for complete search history.

(56) References Cited

U.S. PATENT DOCUMENTS

| 2013/0066193 A1 | 3/2013 | Olson et al. |
| 2018/0132753 A1 | 5/2018 | Schweitzer et al. |
| 2019/0117113 A1 | 4/2019 | Curran |

FOREIGN PATENT DOCUMENTS

| CN | 104170225 A | 11/2014 |
| CN | 104825156 A | 8/2015 |
| CN | 107847745 A | 3/2018 |
| CN | 109965875 A | 7/2019 |
| JP | 2013536011 A | 9/2013 |
| JP | 2014530030 A | 11/2014 |

OTHER PUBLICATIONS

"Communication Pursuant to Article 94(3) EPC Received mailed on Jun. 6, 2023", 6 Pages.
"Notice of Reasons for Rejection Received for Japanese Application No. 2021-571773 mailed on Apr. 4, 2023", 3 Pages.
"Non-Final Office Action Mailed on Jan. 29, 2024", 11 Pages.
"Search Report Mailed on Aug. 2, 2024", 4 Pages.

SYSTEM AND METHOD FOR NOISE TOLERANT CARDIAC LOCALIZATION, NAVIGATION AND MAPPING

This application is a National Stage Application of PCT/US2020/042177, filed on Jul. 15, 2020, which claims benefit of U.S. Provisional Application No. 62/875,557, filed on Jul. 18, 2019, and which applications are incorporated herein by reference. A claim of priority to all, to the extent appropriate, is made.

FIELD

The present disclosure relates to electrical impedance-based measurement of electrodes of a medical device in conjunction with magnetic-based measurement of magnetic sensors of the medical device to provide, among other things, device localization, intracardiac mapping and/or indications of contact between tissue and electrodes of the medical device. More specifically, the disclosure relates to interleaving magnetic measurements with impedance measurements in a manner that reduces noise in the impedance measurements.

BACKGROUND

Catheters are used to perform a variety of tasks within human bodies and other bodies including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and/or to deliver ablative energy to cardiac tissue, among other tasks. In order to properly administer treatment, the position and orientation of a catheter inside the body must be continuously monitored. One known technique for determining the position and orientation of a catheter within a body is by tracking a plurality of sensors on the catheter using a position sensing and navigation system (sometimes called a localization system). In one exemplary system offered for sale by Abbot Laboratories, under the trademark ENSITE™ VELOCITY™, the sensors comprise electrodes. Such a localization system may be referred to as an electric field-based or impedance-based localization system. In such a system, excitation of pairs of electrodes on the outer surface of the body generates electrical fields within the body. Voltage measurements of catheter electrodes can then be used to determine the position and orientation of the catheter electrodes within a coordinate system of the localization system.

Another technique for determining the position and orientation of a catheter inside the body utilizes magnetic sensors and a magnetic field-based localization system. In such a system, a magnetic field generator may create a magnetic field within the body and to control the strength, orientation, and frequency of the field. The magnetic field(s) are generated by coils of the magnetic field generator and current or voltage measurements for one or more magnetic position sensors (e.g., magnetic field sensors) associated with the catheter are obtained. The measured currents or voltages are proportional to the distance of the sensors from the coils thereby allowing for determining a position of the sensors within a coordinate system of the magnetic field-based localization system.

A combined localization system combines an impedance-based system with a magnetic field-based system. Such a system is sold by Abbott Laboratories under the trademark Ensite Precision™. In such a system, locations of electrodes may be identified in an impedance-based coordinate system in conjunction with identifying the locations of one or more magnetic sensors in a magnetic-based coordinate system. In an embodiment, at least a portion of the electrodes and magnetic sensors may be co-located to define fiducial pairs. This co-location allows for determining a transformation (e.g., transformation matrix) between the coordinate systems. The transformation may be applied to the locations of any electrode to register these locations in the generally more accurate magnetic-based coordinate system once the transformation is determined. Accordingly, the impedance-based electrodes can be identified in the coordinate system of the magnetic field-based localization system thereby increasing the positioning accuracy for the electrodes.

The combined medical positioning system, while providing improved accuracy, has a number of shortcomings. For instance, impedance-based medical localization systems are subject to various types of interference that can impact the accuracy of position measurements. For example, the level of electrical impedance in the patient body is not necessarily constant. Further, the impedance-based system and the magnetic-field system are not, from an electrical standpoint, totally independent. Specifically, operation of the magnetic field-based system can induce noise into the measurements of the impedance-based system. To counteract such induced noise, prior systems have temporally alternated the operation and data collection of the two systems. However, such alternating operation is not feasible for an impedance-based localization system that operates continuously.

BRIEF SUMMARY OF THE DISCLOSURE

In an aspect, a position sensing and navigation system is provided for measuring responses of electrodes and, in further arrangements, magnetic sensors of a medical device (e.g., catheter). The system includes an impedance-based localization system. Such an impedance-based localization system may include a signal generator configured to generate a plurality of unique drive signals. Each of the unique drive signals may have a unique modulation frequency that is a harmonic of a common base frequency. The signal generator may further be configured to continuously and simultaneously apply each of the plurality of drive signals across an individual pair of electrodes (e.g., surface patch electrodes) to generate an electric field. The impedance-based localization system may also include a measurement circuit for measuring responses (e.g., composite responses to the continuously applied drive signals) of one or more electrodes of a medical device disposed within the electric field. A demodulator is configured simultaneously demodulate the response signal(s) (e.g., composite response signal(s)) for each unique modulation frequency. The demodulator outputs a demodulated data stream that is received by a filter (e.g., down-sampling filter, decimating filter, etc.). The filter outputs impedance-based values proportional to the location of the one or more electrodes for each unique frequency. The impedance-based values may be utilized to render an image of the medical device and/or its surroundings (e.g., heart chamber). To reduce noise in the impedance-based values, a controller may pause input (e.g., skip data input) into the filter during the operation of an electrical noise generating device (e.g., magnetic localization system) such that portion of the demodulated data stream corrupted by electrical noise is discarded. In an embodiment, the input into the filter is paused for a time period that is an integer multiple of the common base frequency (i.e., of the unique modulation frequencies/drive signals). Use of such a time period allows resuming processing of the demodulated data stream without frequency interruption.

In a further arrangement, the system may include a magnetic localization system for use in identifying the location of one or more magnetic sensors of the medical device. The magnetic localization system may include a magnetic field generator for generating a magnetic field. A measurement circuit may measure the magnetic response of one or more magnetic sensors to the magnetic field to generate location information that may be utilized to, for example, render an image of the medical device and/or its surroundings (e.g., heart chamber). The magnetic localization system may be configured to operate (e.g., under control of a controller) while the input to the decimating filter of the impedance-based localization system is paused.

In an arrangement, the system utilizes digital signal processing where the drive signals are digital drive signals. In such an arrangement, the digital drive signals are converted to analog signals by one or more digital-to-analog (DAC) converters prior application across the individual pairs of electrodes. Likewise, one or more analog-to-digital (ADC) converters may convert analog responses of the electrodes to digital response signals. Is such an arrangement, the time period associated with the pause into the decimating filer is measured in discrete ADC samples.

In another arrangement, the system is configured to detect anomalous events that corrupt a measured response signal and discard the data acquired during the anomalous event to prevent corruption in the impedance-based values. In such an arrangement, the system includes a detector configured to analyze digital samples of the response signal prior to entry of the digital samples into the demodulator. The detector may analyze the digital samples on a sample-to-sample based. For instance, the detector may compare the slew rate of the signals to a predetermined threshold to determine the existence of an anomalous event in the response signal. If an anomalous event is detected, the data input into the filter may be paused for a time period (e.g., an integer multiple of the common base frequency) to effectively discard corrupted data. To prevent entry of corrupted data into the filter, the system may further include a buffer that stores a predetermined set of digital sample prior to their entry into the demodulator. Such a buffer may allow identifying an anomalous event and provide enough time to pause/skip input of the demodulated data stream into the filter.

In another aspect, method for use in sensing the position of elongated medical device within a body of a patient is provided. Generally, the method is used with an impedance-based localization system to reduce noise in impedance measurements caused by electric noise generating devices and/or anomalous events. The method includes generating a plurality of unique drive signals each having a unique modulation frequency that is a harmonic of a common base frequency. The drive signals are each simultaneously and continuously applied across a corresponding pair of electrodes (e.g., surface patch electrodes) to generate an electric field. A composite response signal is measured for one or more electrodes of a medical device disposed within the electric field. The composite response signal(s) is synchronously demodulated to generate a demodulated data stream. The demodulated data stream is paused during electric noise generating events during which the data of the data stream is discarded. The remaining demodulated data stream is filtered (e.g., down-sampled, decimated etc.) to output impedance-based values proportional to the location of the one or more electrodes for each unique drive signal. The impedance-based values may be utilized to render an image of the medical device and/or its surroundings (e.g., heart chamber).

The demodulated data stream may be paused at any time. However, each pause will be for a time period that is an integer multiple of the of the common base frequency (i.e., of the unique modulation frequencies/drive signals). Use of such a time period allows resuming processing (e.g., filtering) of the demodulated data stream without frequency interruption. The demodulated data stream may be paused on a predetermined schedule (e.g., duty cycle) to allow the operation of another noise generating device. For example, on a 1:1 duty cycle, the impedance-based localization system may operate half of the time while another noise generating device (e.g., magnetic localization system) operates the other half of the time. Other duty cycles (e.g., 1:2; 2:1, 3:1 etc.) are possible. However, all cycles will have a time period that is an integer multiple of the common base frequency of the drive signals. In a further arrangement, the demodulated data stream may be paused for a time period upon identifying an anomalous event.

The foregoing and other aspects, features, details, utilities and advantages of the present disclosure will be apparent from reading the following description and claims, and from reviewing the accompanying drawings.

DETAILED DESCRIPTION

Figure 1:
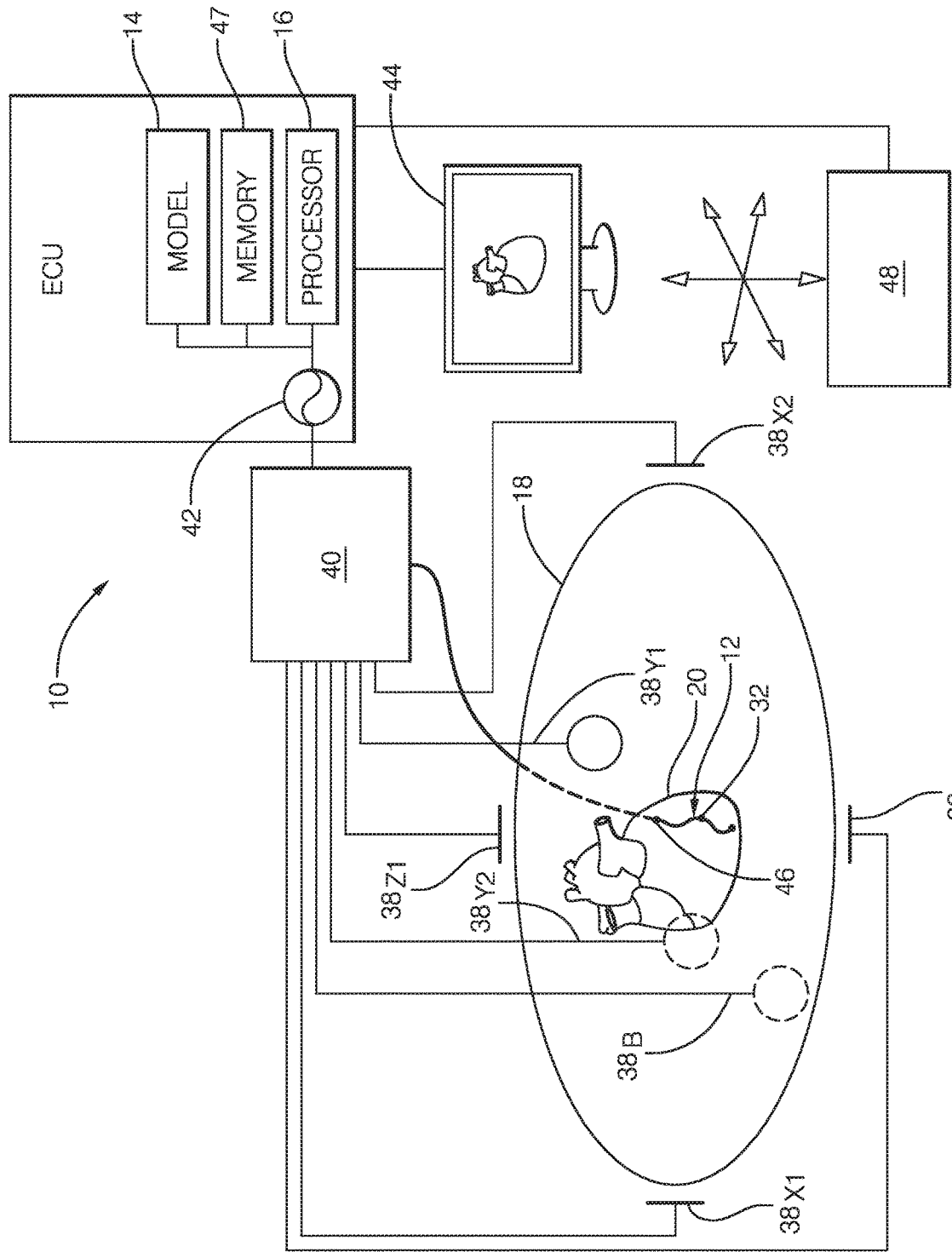
FIG. 1 is a diagrammatic view of one embodiment of combined localization system combines an impedance-based system with a magnetic field-based system.

Referring now to the drawings wherein like reference numerals are used to identify identical components in the various views, FIG. 1 illustrates one exemplary embodiment of a position sensing and navigation system 10 (e.g., localization system) for use in navigating an elongated medical device within a body of a patient and generating an image of the device within the body of the patient. As illustrated, the localization system is a combined localization system that acquires impedance measurement as well as magnetic measurements. In this embodiment, the system 10 includes, among other components, a model construction system 14 and processor apparatus attached to an elongate medical device 12. In this embodiment, the elongated medical device is a catheter 12. The processing apparatus 16 may take the form of an Electronic Control Unit (ECU), for example, that is configured to generate and render an image of catheter 12 and output the image of the catheter to a display 44. The system 10 may further include a user input device (not shown). Although the system is described in terms of rendering a catheter, it should be understood that various elongate medical devices (e.g., introducer sheaths, pacing leads, etc.) could be rendered using the system.

Figure 2:
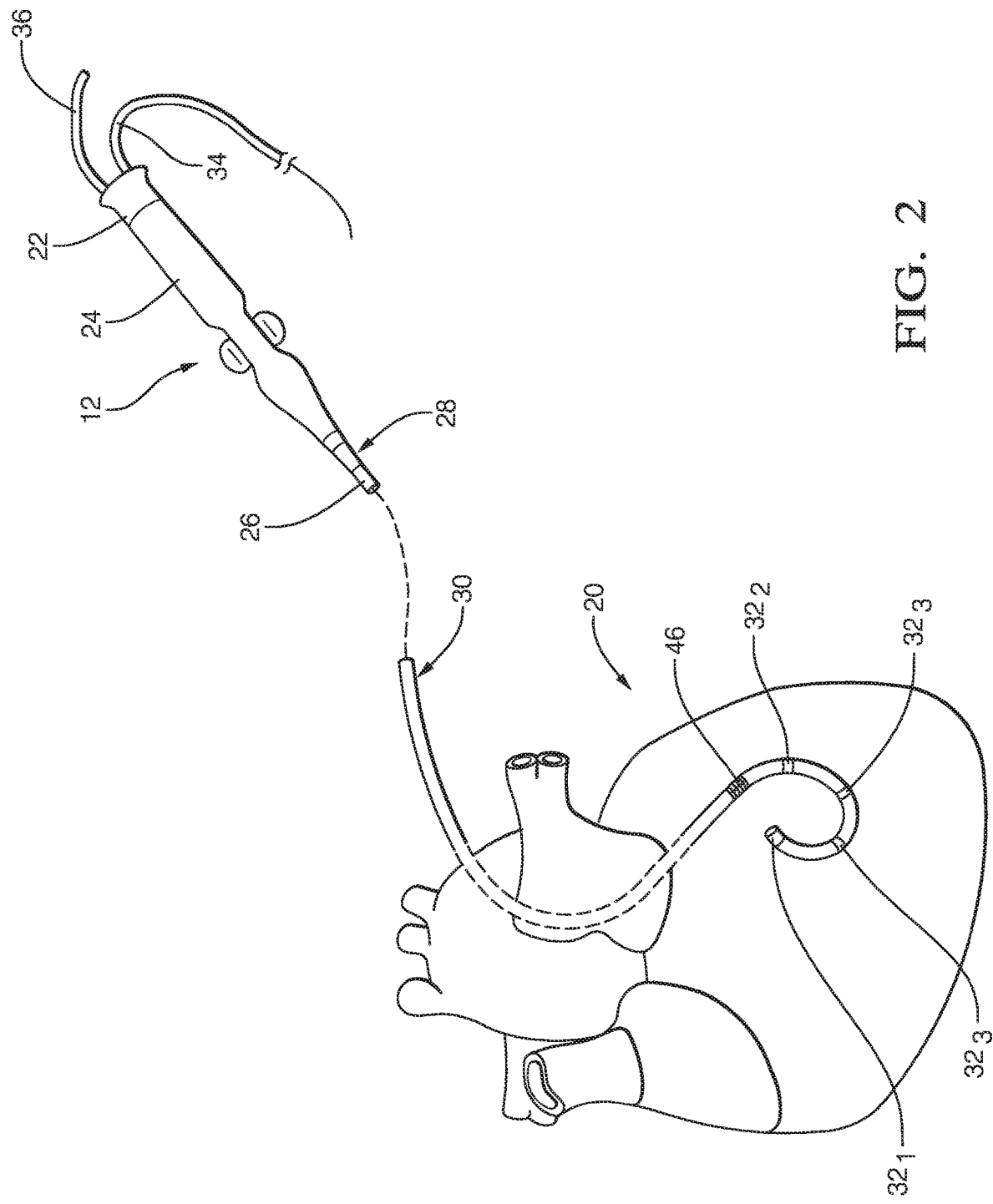
FIG. 2 is a diagrammatic view of a catheter used in the system shown in FIG. 1.

As illustrated in FIGS. 1 and 2, the catheter 12 is configured to be inserted into a patient's body 18, and more particularly, into the patient's heart 20. The catheter 12 may include a cable connector or interface 22, a handle 24, a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient. The connector 22 provides mechanical, fluid, and electrical connection(s) for cables, such as, for example, cables 34, 36 extending to the ECU and/or other components of system 10 (e.g., a visualization, navigation, and/or mapping system, ablation generator, irrigation source, etc.). The handle 24, which is disposed at the proximal end 28 of the shaft 26, provides a location for the clinician to hold the catheter 12 and may further provide means for steering or guiding the shaft 26 within the body 18 of the patient. The catheter 12 may comprise an electrophysiological (EP) catheter for use in gathering EP data associated with the heart 20 to enable generation of an image of the geometry of the heart surface and related EP data. The catheter 12 may also allow removal of bodily fluids or injection of fluids and medicine into the body and may further provide a means for transporting surgical tools or instruments within a body including those used for pacing or tissue ablation. Although the catheter 12 is described as an EP catheter in an embodiment, it should be understood that the system can be used with a variety of different types of catheters including, for example, intracardiac echocardiography (ICE) catheters and ablation catheters using a wide variety of ablative energies (e.g., radiofrequency, cryogenic, ultrasound, laser or other light, etc.).

As best shown in FIG. 2, the catheter 12 may include a plurality of electrodes 32 such as distal tip electrode $32_1$, proximal ring electrode $32_2$, and intermediate ring electrodes $32_3$ (hereafter '32' unless specifically referenced). The electrodes 32 are provided to generate information regarding the position of catheter 12 and therefore may function as position sensors. The electrodes 32 may also provide information regarding the geometry of the heart 20. The catheter 12 may also include one or more magnetic position sensor(s) 46. The magnetic position sensor(s) 46 are also provided for use in determining the position of the catheter 12 within a body. In the illustrated embodiment, the magnetic sensor 46 is disposed within the shaft of the catheter and is formed of a coil. However, it should be understood that the magnetic sensor(s) sensors may take other forms. That is the magnetic sensor(s) may, for example, comprise any conventional position sensors for detecting changes in magnetic fields including Hall effect sensors, magnetoresistive sensors and sensors made from magnetoresistive materials, piezoelectric materials and the like. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

Referring again to FIG. 1, the system further includes a plurality of patch electrodes 38, a multiplex switch 40, and a signal generator 42 (e.g., frequency source) that, in conjunction with the processor 16, collectively define an impedance-based localization system. Other components are possible. The processing apparatus 16 may include a programmable microprocessor or microcontroller, or may include an application specific integrated circuit (ASIC). Further, the processing apparatus 16 may include a central processing unit (CPU) and an input/output (I/O) interface through which the processing apparatus 16 may receive a plurality of input signals including, for example, signals generated by patch electrodes 38 and the position sensors 32 (e.g., catheter electrodes). Further the processing apparatus may generate a plurality of output signals including, for example, those used to control and/or provide data to, for example, display device 44 and switch 40. The processing apparatus 16 may be configured to perform various functions, such as those described in greater detail below, with appropriate programming instructions or code (i.e., software). Accordingly, the processing apparatus 16 is programmed with one or more computer programs encoded on a computer storage medium for performing the functionality described herein.

With the exception of reference patch electrode $38_B$ called a "belly patch electrode," the patch electrodes 38 are provided to generate electrical signals used, for example, in determining the position and orientation of the catheter 12 within a three-dimensional coordinate system and in generating EP data regarding the heart 20. In one embodiment, patch electrodes 38 are placed orthogonally on the surface of the body 18 and are used to create axes-specific electric fields within body 18. For instance, in one embodiment, patch electrodes $38_{X1}$, $38_{X2}$ may be placed along a first (x) axis. Patch electrodes $38_{Y1}$, $38_{Y2}$ may be placed along a second (y) axis, and patch electrodes $38_{Z1}$, $38_{Z2}$ may be placed along a third (z) axis. In addition, a reference electrode (e.g., $38_B$) is attached to body 18. Each of patch electrodes 38 may be coupled to multiplex switch 40. In this embodiment, the processing apparatus 16 is configured, through appropriate software, to provide control signals to the switch 40 to thereby sequentially couple pairs of electrodes 38 to the signal generator 42. Excitation of each pair of electrodes 38 generates an electric field within the body 18 and within an area of interest such as the heart 20. Voltage levels at non-excited electrodes 38, which are referenced to the belly patch electrode $38_B$, are filtered and converted and provided to the processing apparatus 16 for use as reference values.

Electrodes 32 on the catheter 12 are disposed within electrical fields created in body 18 (e.g., within the heart 20) by exciting the patch electrodes 38. These electrodes 32 experience voltages that are dependent on the location between the patch electrodes 38 and the position of the electrodes 32 relative to the surface of the heart 20. Voltage measurement comparisons (e.g., impedance responses) can be used to determine the position of the electrodes 32 within the heart 20. Movement of the electrodes 32 within the heart 20 (e.g., within a heart chamber) produces information regarding the geometry of the heart 20, EP data as well as location information for the catheter. Though discussed with respect to an orthogonal arrangement of patch electrodes 38, the present disclosure is not meant to be so limited. Rather, in other embodiments, non-orthogonal arrangements (e.g., arrangements of non-orthogonal dipoles) may be utilized to determine the location coordinates (e.g., positions) of the electrodes 32.

The system 10 determines the position and orientation of position sensors such as the electrodes 32 on an elongate medical device such as the catheter 12. The model construction system 14 uses this position and orientation data to generate an image of the catheter 12 within the heart 20. More particularly, the processing apparatus 16 of the model construction system 14 is configured to acquire measured data points (e.g., impedance responses) collected using the position sensors (i.e., electrodes 32), where the measured data points corresponding to respective positions of electrodes 32. In this embodiment, the model construction system 14 acquires the measured data points by activating electrodes 32 as described above. Generally, the model construction system 14 is configured to describe the measured data points as deviations from a parametric form (e.g., a curve, in the case of a one-dimensional catheter 12, or a plane, in the case of a two-dimensional catheter 12) and generate an image of the catheter using such deviations. Stated otherwise, the model construction system utilizes the measured data points with a mathematical model that describes a particular catheter supporting the electrodes to generate an image of that catheter based on the positions of the data points. One exemplary model construction system is set forth in U.S. Pat. Pub No. 2018/0014751 entitled "Methods and Systems for Generating Smoothed Images of an Elongate Medical Device" the entire disclosure of which is incorporated herein by reference.

As further shown in FIG. 1, the system 10 may further incorporate a magnetic field-based localization system to determine the position and orientation of a catheter and/or similar medical devices within a body. In such a system, a magnetic field generator 48 may be employed having three orthogonally arranged coils, arranged to create a magnetic field within the body and to control the strength, orientation, and frequency of the field. Alternately, the magnetic field generator 48 may have more than three coils, and such coils may by arranged in pseudo-random orientations. The magnetic field generator 48 may be located above or below the patient (e.g., under a patient table) or in another appropriate location. Magnetic fields are generated by coils of the magnetic field generator and current or voltage measurements for one or more magnetic position sensors 46 (e.g., magnetic field sensors) associated with the catheter 12 are obtained. The measured currents or voltages of the sensors 46 are proportional to the distance of the sensors from the coils thereby allowing a position of the sensors within a coordinate system of the system. The positions of the sensors may be utilized by the model construction system to generate an image of the medical device on a display relative to, for example only, a cardiac model or geometry. Exemplary embodiments of magnetic field-based medical positioning systems are set forth in co-owned U.S. Pat. No. 7,386,339 and U.S. Pat. App. No 2013/0066193, hereby incorporated by reference in their entirety.

When utilizing a dual electric field-based system (e.g., impedance-based system) and magnetic field-based system, the system 10 may utilize, for example, the EnSite Precision™ system commercially available from Abbott Laboratories, and generally shown with reference to U.S. Pat. No. 7,263,397 entitled "Method and Apparatus for Catheter Navigation and Location and Mapping in the Heart", the entire disclosure of which is incorporated herein by reference. In other embodiments, however, the system 10 may comprise other types of systems, such as, for example and without limitation: a magnetic-field based system such as the Carto™ system available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster; as well as other impedance-based localization systems, acoustic or ultrasound-based systems, and commonly available fluoroscopic, computed tomography (CT), and magnetic resonance imaging (MRI)-based systems.

In summary, the electrodes 32 and/or magnetic sensors 46 of the catheter 12 are electrically coupled to the processing apparatus 16 and are configured to serve a position sensing function. The electrodes 32 and/or magnetic sensor(s) 46 are placed within electric and/or magnetic fields created in the body 18 (e.g., within the heart) by sequentially exciting the patch electrodes 38 and/or operating the magnetic field generator 48. Using various known algorithms, the processing apparatus 16 may then determine the location (position and orientation) of each electrode 32 and/or magnetic sensor 46 and record it as a measured data point corresponding to a respective position of each sensor in a memory or storage device, such as a memory 8, associated with or accessible by the processing apparatus 16. These data points may then be utilized by the model construction system to generate an image of the catheter and/or to generate a map of an interior patient cavity (e.g., heart chamber).

The impedance-based localization system provides the ability to simultaneously locate a relatively large number of electrodes and has found widespread acceptance and use in the industry. However, because impedance-based systems employ electrical current flow in the human body, these systems can be subject to measurement inaccuracies and efforts have been made to combine impedance-based localization systems with magnetic-based localization systems to improve overall accuracy. However, operation of the magnetic-based localization systems (e.g., magnetic field generator) can induce electrical interference that affect impedance measurements. Accordingly, prior systems have typically interleaved the operation of the impedance-based systems and the magnetic-based system to reduce such interference. By way of example, prior systems sequentially couple the patch electrodes 38 to the signal generator 42 for impedance measurement. In such an arrangement, the magnetic-based system may operate between the sequential operation of the patch electrodes minimizing electrical interference. While such operation is effective in reducing electrical interference in the impedance measurements, such operation is only possible if operation of the patch electrodes is discontinuous.

Aspects of the present disclosure are further based on the recognition that simultaneously and continuously application of separate unique frequency drive signals (e.g., localization frequencies or modulation frequencies) to the patch electrodes results in location impedance values (e.g., measured impedance values of catheter electrodes in response to being driven by the external patch electrodes) having lower noise levels. In such an arrangement, the patch electrodes are driven continuously rather than being sequentially coupled to a signal generator for impedance location measurements. Use of such continuous unique modulation frequencies not only allows for achieving low noise impedance values but also minimizes crosstalk between channels.

To achieve such low noise impedance location values, continuous unique frequency drive signals (e.g., modulation frequencies) may be utilized. For example, three continuous unique drive frequencies may be utilized where one unique frequency is applied to each patient axis (e.g., $38_{X1}$-$38_{X2}$; $38_{Y1}$-$38_{Y2}$ and $38_{Z1}$-$38_{Z2}$). The signal processing system uses modulation frequencies that are orthogonal. That is, modulation frequencies that are multiples of a common base frequency. This provides modulation frequencies that are close in value (expressed in cycles per second or Hertz) and that do not interfere with one another. The period of the base frequency determines a time interval in which all the modulation frequencies are periodic. For example, if the base frequency is 100 Hz, the base period is 1/100 seconds or 10 milliseconds (ms). At a point in time, any of the modulation frequencies will return to the same point cycle every 10 ms. For example, frequencies of 7900, 8000 and 8100 Hz all have a common base frequency of 100 and any 10 ms interval will contain exactly 79, 80 or 81 cycles, respectively. Such an interval may start at any arbitrary point and will repeat an identical point in each of the modulation frequencies, as discussed herein.

A system that simultaneously and continuously applies separate unique frequency drive signals system utilizes synchronous excitation and synchronous demodulation along with a filtering method that is compatible with orthogonal modulation frequencies. In such a system, a demodulator multiplies the sensor signal (e.g. composite measured signal of each catheter electrode in response to the multiple modulation signals/frequencies) received from an analog-to-digital converter (ADC) by each of the modulation frequencies, on a sample by sample basis. A filter essentially averages the demodulator outputs, one for each modulation frequency, over the base period and provides a result at a rate substantially reduced (down sampled or decimated) from the original A/D sample rate. In an embodiment, the filter is a cascade integrator-comb (CIC) filter. The output rate is the same as base frequency, in this example 100 times per second. The result is a set of values proportional to the location of the electrode in each axis (e.g., an X, Y, Z coordinate).

Synchronous demodulation allows the responses to the unique modulation frequencies to be detected independent of each other while minimizing crosstalk. As previously noted, synchronous demodulation includes multiplying the measured and digitized response signal (which is a composite of multiple modulation frequencies) by a replica of each drive signal of exactly the same frequency and a known phase offset. The resultant signal is then low-pass filtered and decimated to (in this example) 100 samples per second. The sampling rate of the analog-to digital converter (ADC) is not critical and in fact need not meet the traditional Nyquist sampling rate. However, the amplifying circuit must have adequate bandwidth to pass the signal to the ADC. By calibrating the system and compensating for expected phase delay between drive signal and received signal, quadrature demodulation may occur. Thus, a real component for resistive impedance and an imaginary component for reactive impedance may be found. This is commonly known as complex impedance. Synchronous demodulation also allows for signal extraction with very low current levels though higher current levels provide better signal-to-noise ratio.

Figure 3:
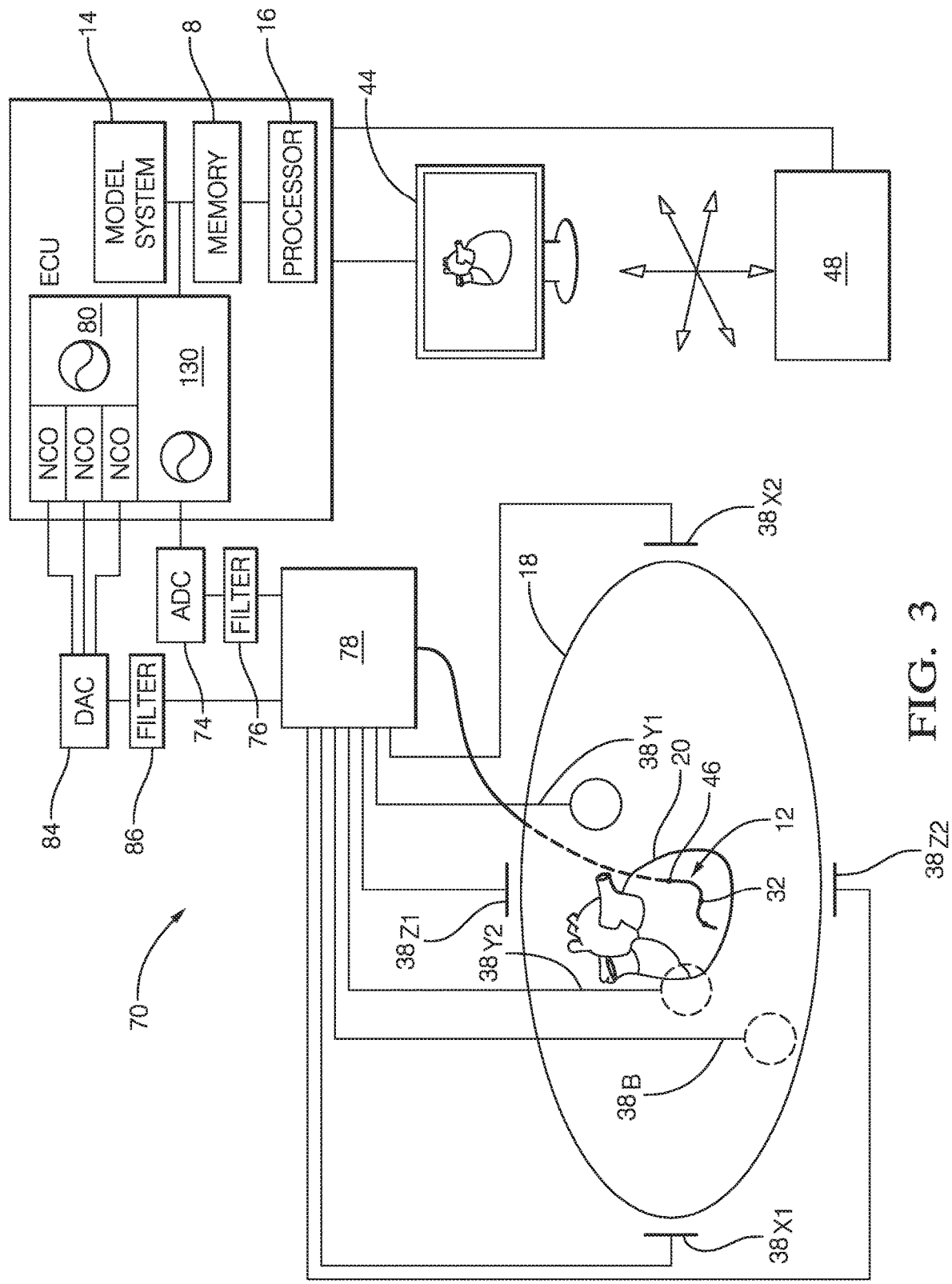
FIG. 3 is a diagrammatic view of another embodiment of combined localization system combines an impedance-based system with a magnetic field-based system.

FIG. 3 is a diagrammatic depiction of an embodiment of a combined localization system 70 that is configured to synchronously excite electrodes at unique modulation frequencies (e.g., patch electrodes 38 and/or catheter electrodes 32) and synchronously demodulate responses of such electrodes. The system is similar to the system described in FIG. 1 and similar components utilize common reference numbers. In addition to the components described in relation to FIG. 1, the system 70 includes an analog-to-digital converter (A-to-D) 74, a filter 76 (e.g., bandpass filter), a digital to analog converter 84, a filter 86 (e.g., bandpass filter), a multifrequency signal circuit or signal generator 80 and a demodulator circuit or demodulator 130. Additional circuitry and/or components may be included as discussed below in FIGS. 4 and 5. Again, the system 70 may be electronically and/or mechanically coupled with an elongate medical device such as catheter 12. The converters 74, 84, signal generator 80 and demodulator 130 allow the system to simultaneously apply unique drive/excitation signals to the patch electrodes and measure the responses of the catheter electrodes. More specifically, the signal generator 80 outputs multiple orthogonal excitation signals (e.g., modulation or localization frequencies) for use in assessing locations and/or impedances of one or more electrodes. More specifically, the signal generator 80 may generate a plurality of excitation or drive signals each having unique modulation frequencies.

The system 70 again includes a memory 8 and a processor 16. The memory 8 may be configured to store data respective of the elongate medical device or catheter 12, the patient, and/or other data (e.g., calibration data). Such data may be known before a medical procedure (medical device specific data, number of catheter electrodes, etc.), or may be determined and stored during a procedure. The memory may also be configured to store instructions that, when executed by the processor 16, cause the ECU to perform one or more methods, steps, functions, or algorithms described herein. For example, but without limitation, the memory may include data and instructions for determining locations and/or impedances respective of one or more electrodes 32 on the elongate medical device 12.

Figure 4:
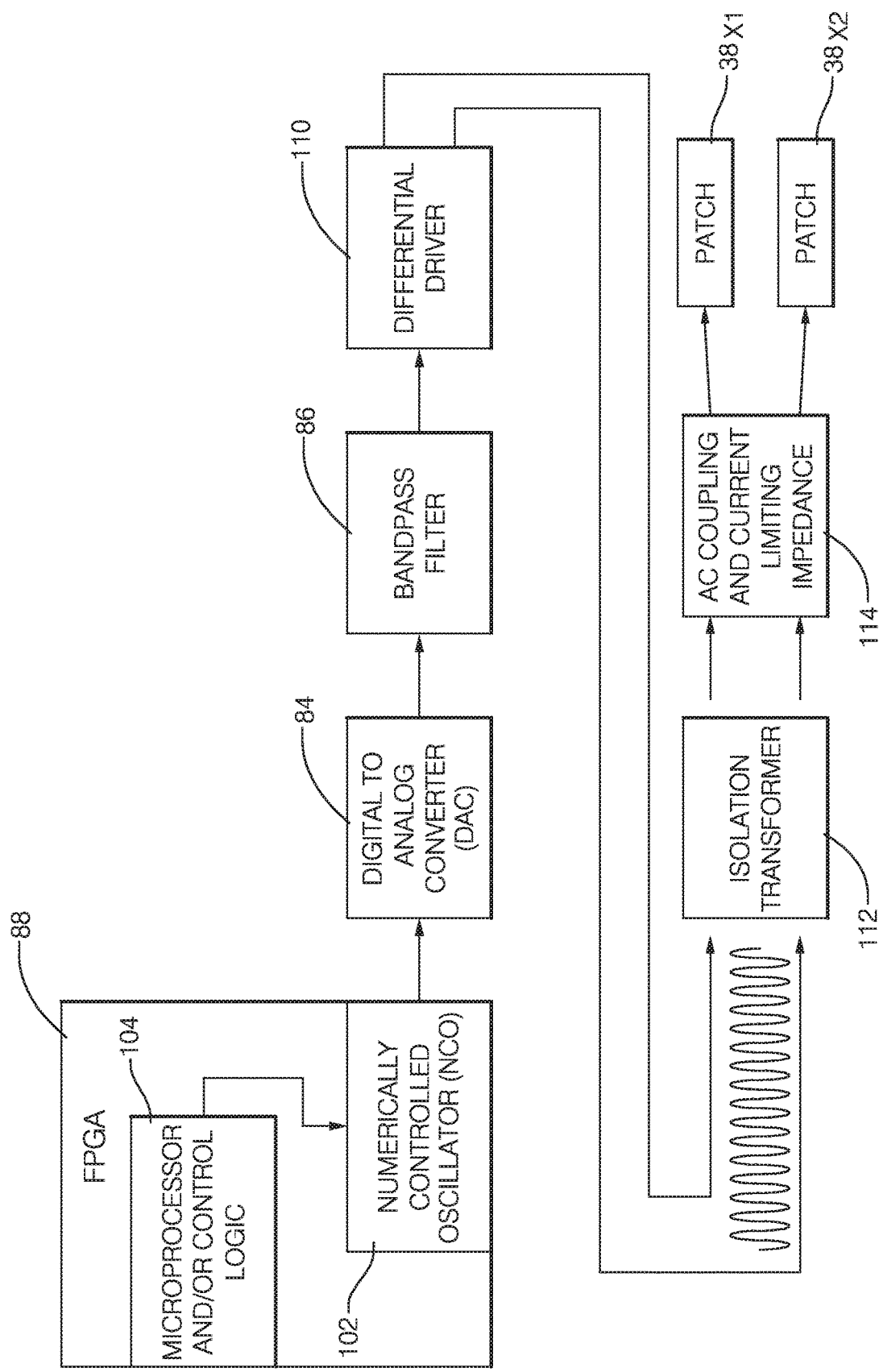
FIG. 4 is a diagrammatic depiction of one embodiment of a signal generator.

FIG. 4 illustrates one embodiment of the signal source 80 (e.g., current source) that provides an excitation signal for one pair of patch electrodes. In the present embodiment, the signal source 80 includes a field programmable gate array (FPGA) 88. However, it will be appreciated that other circuitry, including without limitation, application specific integrated chips, Altera Cyclone series or Xilinx Spartan series may be utilized. In the present embodiment, the FPGA 88 includes a numerically controlled oscillator (NCO) 102. The NCO 102 is a digital signal generator which creates a synchronous (i.e. clocked), discrete-time, discrete-valued representation of a waveform, usually sinusoidal. The NCO 102 is programmable to provide a waveform having a desired frequency, amplitude and/or phase.

In the present embodiment, the NCO 102 creates a sinusoidal waveform of a desired frequency (e.g., modulation frequency) based on an input (e.g., single fixed-frequency reference) provided from a microprocessor and/or control logic 104. In the present embodiment a microprocessor/control logic 104 is incorporated in the FPGA provides the inputs to the NCO 102. However, it will be appreciated that the NCO inputs may be provided by, for example, the processor 16 of the ECU. In any arrangement, the NCO 102 generates a digital waveform output having a desired frequency. The output of the NCO is received by a digital to analog converter (DAC) 84, which converts the received digital signal to a corresponding analog signal. A bandpass filter 86 is utilized to smooth the converted analog signal. A differential driver (e.g., op amp) 110 receives the smoothed analog signal from the bandpass filter 86 and sends the same signal as a differential pair of signals, each in its own conductor to an isolation transformer 112. Provided that impedances in the differential signaling circuit (e.g., differential driver and isolation transformer) are equal, external electromagnetic interference tends to affect both conductors identically. As the receiving circuit (isolation transformer) only detects the difference between the conductors, the technique resists electromagnetic noise compared to a one conductor arrangement. The isolation transformer 112 transfers AC current of the signals originating from the source 80 to the patch electrodes (e.g., $38_{X1}$-$38_{X2}$). The isolation transformer 112 blocks transmission of DC components in the signals from passing to the patch electrodes while allowing AC components in signals to pass. The dual output from the isolation transformer 112 is received by AC coupler 114 (e.g., capacitor) that further limits low frequency current from passing to the patch electrodes. The AC coupler outputs the signals to the patch electrodes.

Figure 5:
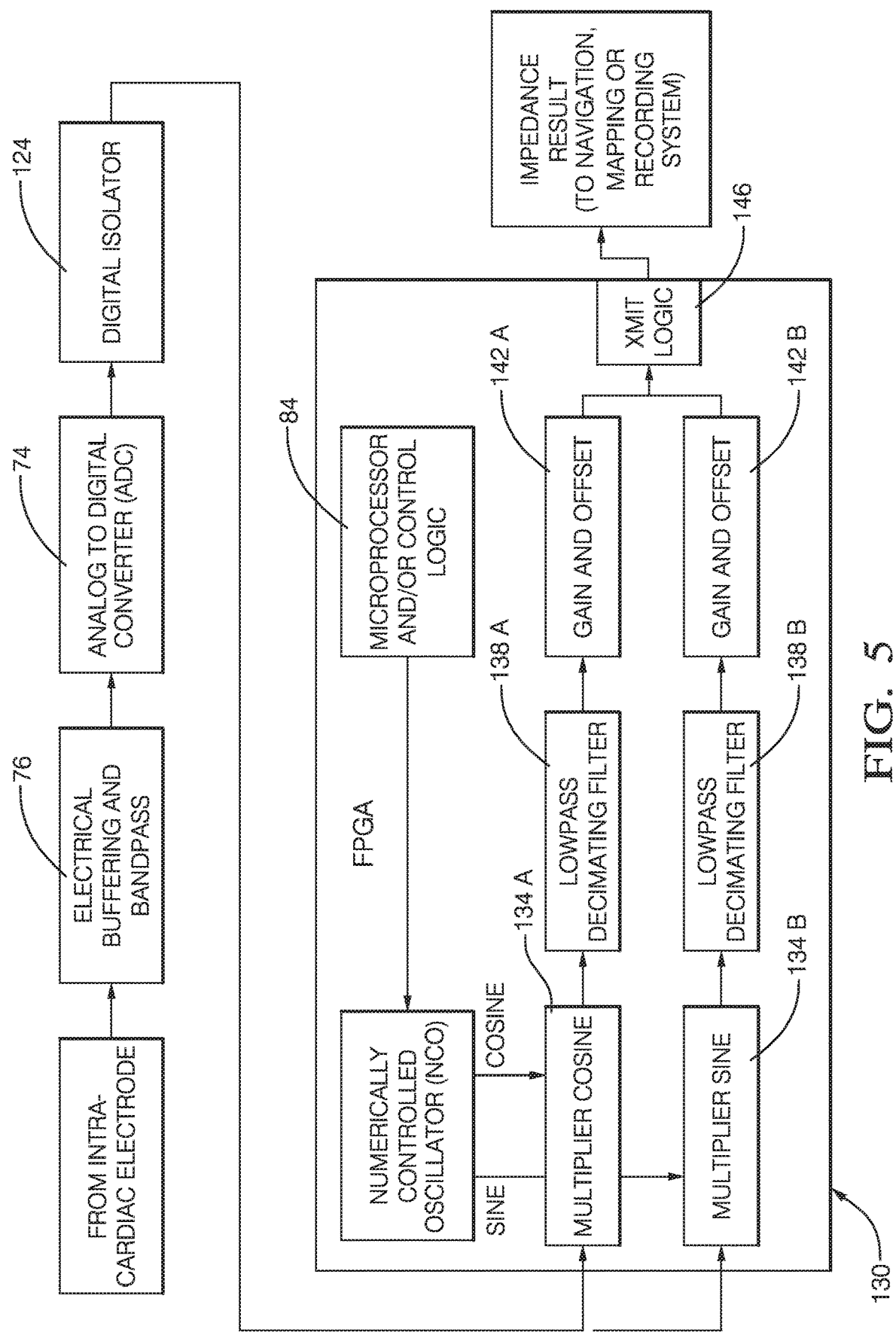
FIG. 5 is a diagrammatic depiction of one embodiment of a measurement circuit and demodulation circuit.

FIG. 5 illustrates one embodiment of a signal measuring circuit (e.g., signal sampler) and a synchronous demodulation circuit. Initially, a response signal (e.g., composite response to the multiple unique modulation frequencies) from one of the catheter electrodes (e.g., intracardiac electrode) is received at a filter 76 (e.g., buffer amplifier) that transfers a current from the electrode, which has a low output impedance level, to an analog to digital converter (ADC) 74, which typically has a high input impedance level. The buffer amplifier prevents the ADC from loading the current of electrode circuit and interfering with its desired operation. The ADC 74 samples the received analog signal at a known sampling rate (e.g., 64 k/s) and converts the analog response signal to a digital response signal. In the present embodiment, an output of the ADC passes through a digital isolator 124, which transfers the digital response signal to the control system (e.g., ECU) while isolating the control system from the medical device.

The digital response signal passes to a synchronous demodulator circuit 130 which, in the present embodiment, is defined in the same FPGA utilized for the signal source 80. As noted, synchronous demodulation consists of multiplying a digitized response signal by a replica of a drive signal of exactly the same frequency and a known phase offset. That is, a demodulation signal having the same frequency as the drive signal (e.g., modulation frequency) and a known phase offset from the drive signal is generated and multiplied with the digitized response signal. Generating the demodulation signal(s) using the same FPGA 88 that generates the drive signal(s) simplifies the demodulation process. However, it will be appreciated that this is not a requirement and that the synchronous demodulator circuit and the signal source may be separate and/or formed of different software and/or hardware components. In any arrangement, the synchronous demodulation circuit must be able to replicate the drive signal for a given unique frequency.

In the illustrated embodiment, the digital response signal is split as it is received by the synchronous demodulator circuit 130. A numerically controlled oscillator (NCO) 132 generates sine and cosine representations of the drive signal (e.g., same frequency different phase) based on an input provided from the microprocessor and/or control logic 104. The split digital response signals are multiplied point-by-point by the sine and cosine signals in sine and cosine multipliers 134A, 134B (hereafter 134 unless specifically referenced). That is, the digital response signals are processed by synchronous multipliers or demodulators. This yields a real (sine) and an imaginary (cosine) channel. The sine and cosine channels are filtered and decimated by low pass decimating filters 138A, 138B, (hereafter 138 unless specifically referenced) which in the present embodiment are formed of cascaded integrator-comb (CIC) filters. Following the example above, where the drive signal is a harmonic of a 100 Hz base frequency, the channels/signals are decimated to 100 samples per second such that each decimated signal has an integer number of cycles. The decimated signals then pass through a gain and offset calibration 142A, 142B to compensate for expected phase delays between the source signal and the response signal. The signals may then be combined. Thus, a real component of resistive impedance and an imaginary component of reactive impedance may be found. This information may then be transmitted, for example, via an output port 146 to, for example, the processor of the ECU. This process is performed (e.g., simultaneously) for each of the three drive frequencies. The ECU may then use this information (impedance location measurements) to generate values proportional to the location of the electrode in each axis (e.g., an X, Y, Z coordinate). Though discussed in relation to determining impedance location measurements, it will be appreciated that the system 70 may also be used to synchronously excite and synchronously demodulate pairs of intracardiac electrodes (e.g., bi-polar electrodes) of the catheter 12.

Figure 6A:
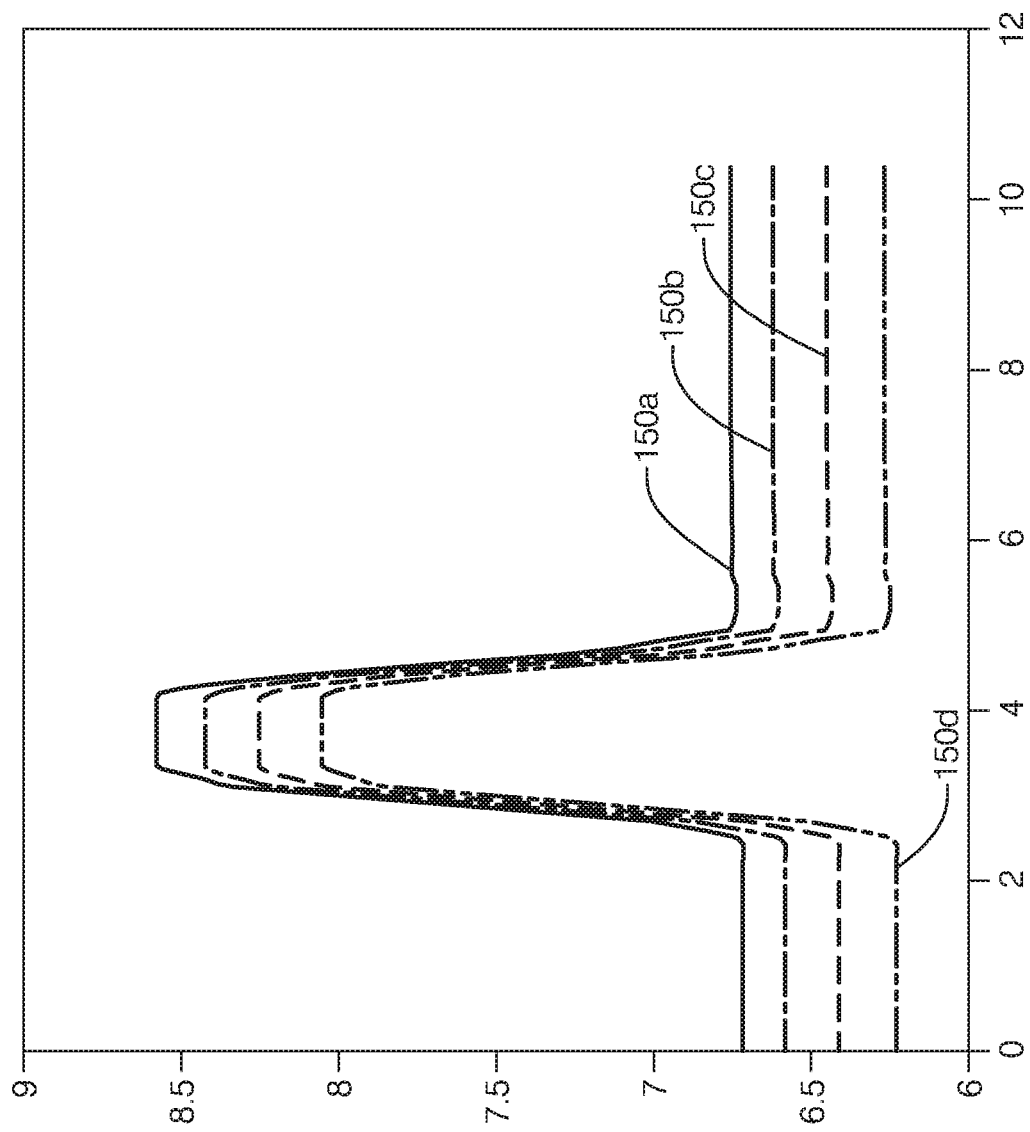
FIGS. 6A-6C illustrate impedance response traces obtained without noise, with noise and with interleaving.
Figure 6B:
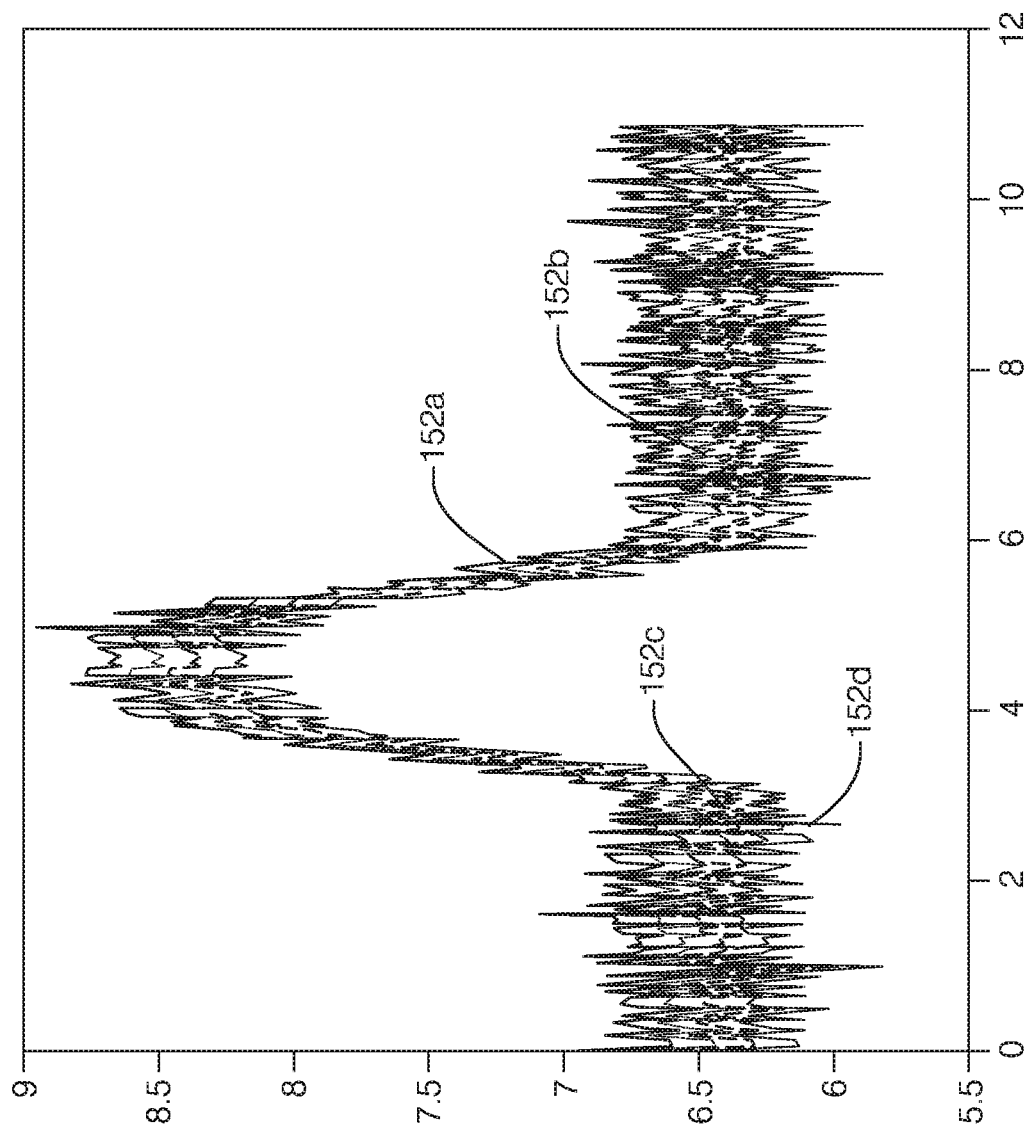

The system 70 described in FIGS. 3-5 allows for continuously exciting the patch electrodes 38 and/or intracardiac electrodes 32 of a catheter to acquire low noise impedance responses. However, operation of the magnetic field-based localization system 40 introduces noise into the acquired impedance responses. That is, operation of the magnetic field-based localization system affects the impedance responses acquired by the impedance-based localization system, which continuously excites (e.g., applies drive signals) the patch electrodes and/or intracardiac electrodes. This is graphically illustrated in FIGS. 6A and 6B. FIG. 6A illustrates impedance location values (e.g., ohms vertical axis) monitored over time (horizontal axis) of four catheter electrodes in a saline tank where the impedance values are acquired by an impedance-based localization system that continuously drives patch electrodes. As illustrated, the impedance location values over time or "location traces" 150a-d identify the position of the four catheter electrodes in a vertical axis. In this example, the catheter electrodes move from a stationary position upward approximately four inches and then back to the stationary position. As shown, each of the traces 150a-d is a substantially smooth line corresponding with low noise. FIG. 6B illustrates the same movement of the catheter electrodes and corresponding location traces 152a-d obtained by the same impedance-based localization during the operation of a magnetic field-based localization system. As shown, each of the traces 152 is distorted as noise from the operation of the magnetic field-based localization system corrupts the impedance location values obtained by the impedance-based localization system. Rendering an image of, for example, a catheter using such data would result in a shaky image requiring significant display filtering. Further, due to the continuous application of drive signals to the patch electrodes, there is no opportunity to operate the magnetic field-based localization system between application of electrode drive signals unlike prior systems, which sequentially drive the electrodes.

To counter the effects of the operation of a magnetic field-based localization system on impedance responses acquired by an impedance-based localization system that operates continuously, the combined system operates in a skipping mode. During the skipping mode, the decimating filter(s) (e.g., CIC filter) are starved of noisy data in an incoming data stream (i.e., demodulated data stream) for a predetermined time period. During this time period, the magnetic field-based localization system energizes its magnetic emitters (e.g., coils) and collects data for a location determination. The coils deenergize shortly before the end of the time period at which time the decimating filter resumes processing of the demodulated data stream. While similar in theory to temporally alternating the operation of both localization systems, the impedance-based localization system never ceases operation and continually drives, for example, the patch electrodes. Further, to allow the decimating filter(s) to properly resume operation, the incoming demodulated data stream must be at the exact location in its cycle before the incoming demodulated data stream was paused. Otherwise, the decimating filter will encounter a frequency discontinuity corrupting its output. Utilization of orthogonal frequencies for drive signals provides a means to stop and start the demodulated data stream at the exact same location in its cycle.

Figure 7A:
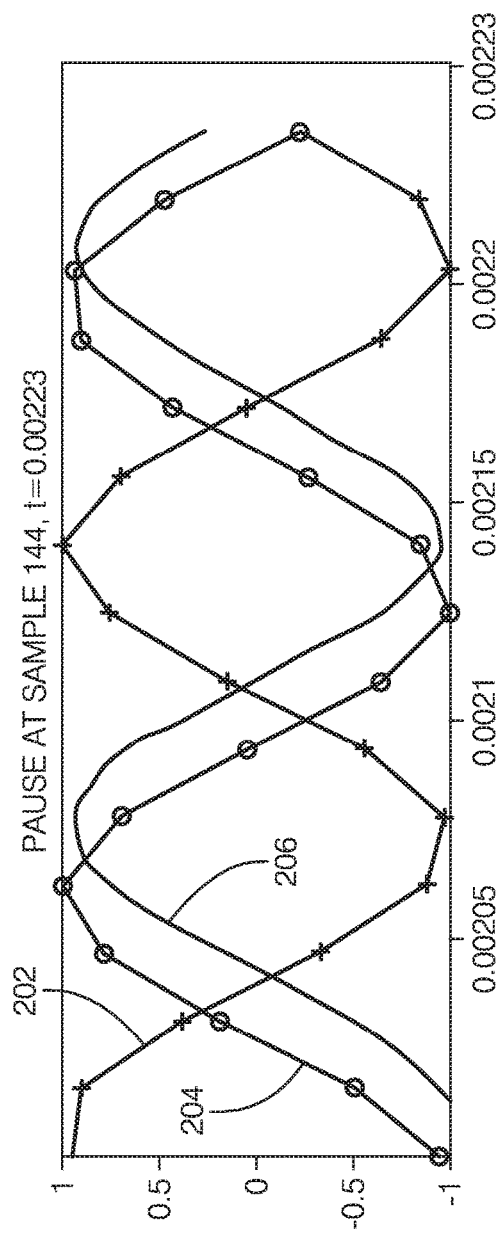
FIGS. 7A and 7B are exemplary depictions of a multi-frequency drive signal and/or response signal.

FIG. 7A illustrates three orthogonal drive signals, which are applied to the three pairs of surface patch electrodes (e.g., $38_{X1}$-$38_{X2}$; $38_{Y1}$-$38_{Y2}$ and $38_{Z1}$-$38_{Z2}$) for electrode localization. In the illustrated embodiment, the first signal 202 has a frequency of 7900 Hz, the second signal 204 has a frequency of 8000 Hz and the third signal 206 has a frequency of 8100 Hz. As previously noted, the frequencies are multiples of a common base frequency of 100 Hz and the period of the base frequency determines a time interval in which all the 'modulation frequencies' are periodic. When the base frequency is 100 Hz, the base period is $\frac{1}{100}$ seconds or 10 milliseconds (ms). At point in time, any of the modulation frequencies will return to the same point cycle every 10 ms. For example, the frequencies of 7900, 8000 and 8100 Hz will all have a common base frequency of 100 and any 10 ms interval will contain exactly 79, 80 or 81 cycles, respectively. Accordingly, if a demodulation data stream into the decimating filter is paused for a time period that is an integer multiple of the base period, resumption of the demodulation data stream into the decimating filter will occur at the exact same location in all of the modulation frequencies.

Figure 7B:
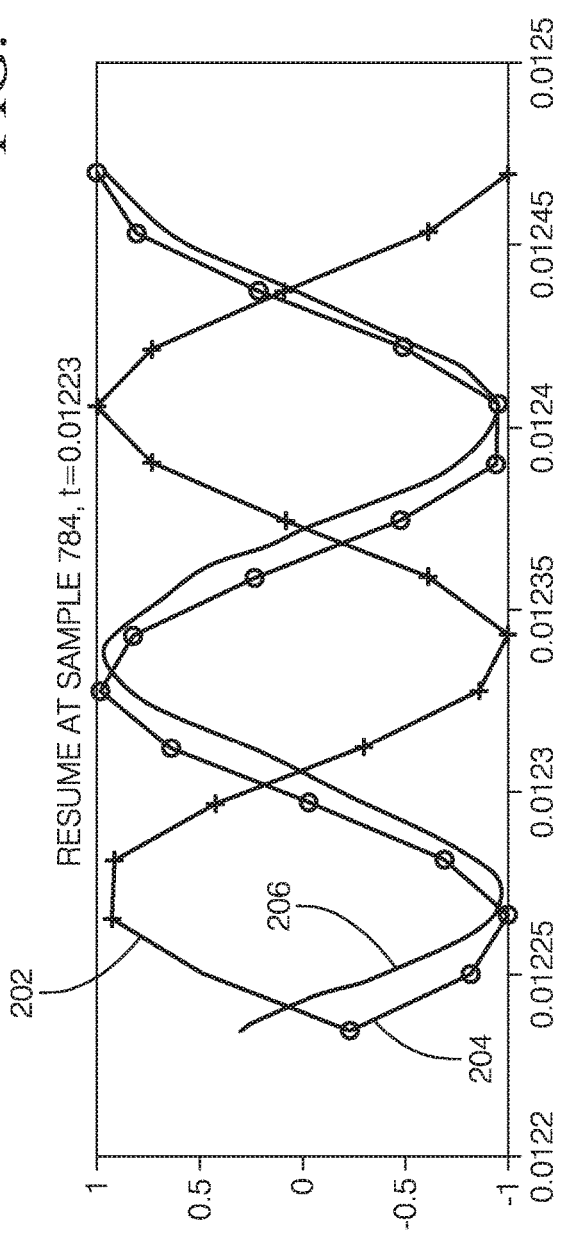

FIGS. 7A and 7B also collectively illustrate an exemplary demodulated data stream of a response signal including information of the three drive signals 162, 164 and 166 as are applied to the patch electrodes. That is, these figures can be used to visualize a response signal from a catheter electrode that is measured in response to the drive signals and converted from an analog signal to a digital signal by and analog to digital converter (ADC). The digital signal is demodulated, which forms the demodulation data stream into the decimating filter(s) (e.g., 138A, 138B). See. e.g., FIG. 5. In the illustrated embodiment, the sample rate of the ADC is 64 k/s such that 640 ADC samples corresponds to a 10 ms base period. As shown in FIG. 7A, the demodulated data stream into the filter(s) is paused/suspended at ADC sample 144 at time 0.00223. FIG. 7B shows the resumption of the demodulated data stream at ADC sample 784 (640 ADC samples after pausing) at time 0.01223 exactly 10 ms (i.e., one base period) after the pause began. As shown, the right edge of the paused signals 202-206 of FIG. 7A match exactly with the left edge of the resumed signals 202-206 of FIG. 7B. Accordingly, upon resumption of the demodulated data stream into the filter, the filter sees no frequency discontinuity. There may, however, be some change in the amplitude in the resumed signals due to, for example, a change in electrode or catheter location, however, such a change is expected to be small due to the short pause interval.

Figure 8:
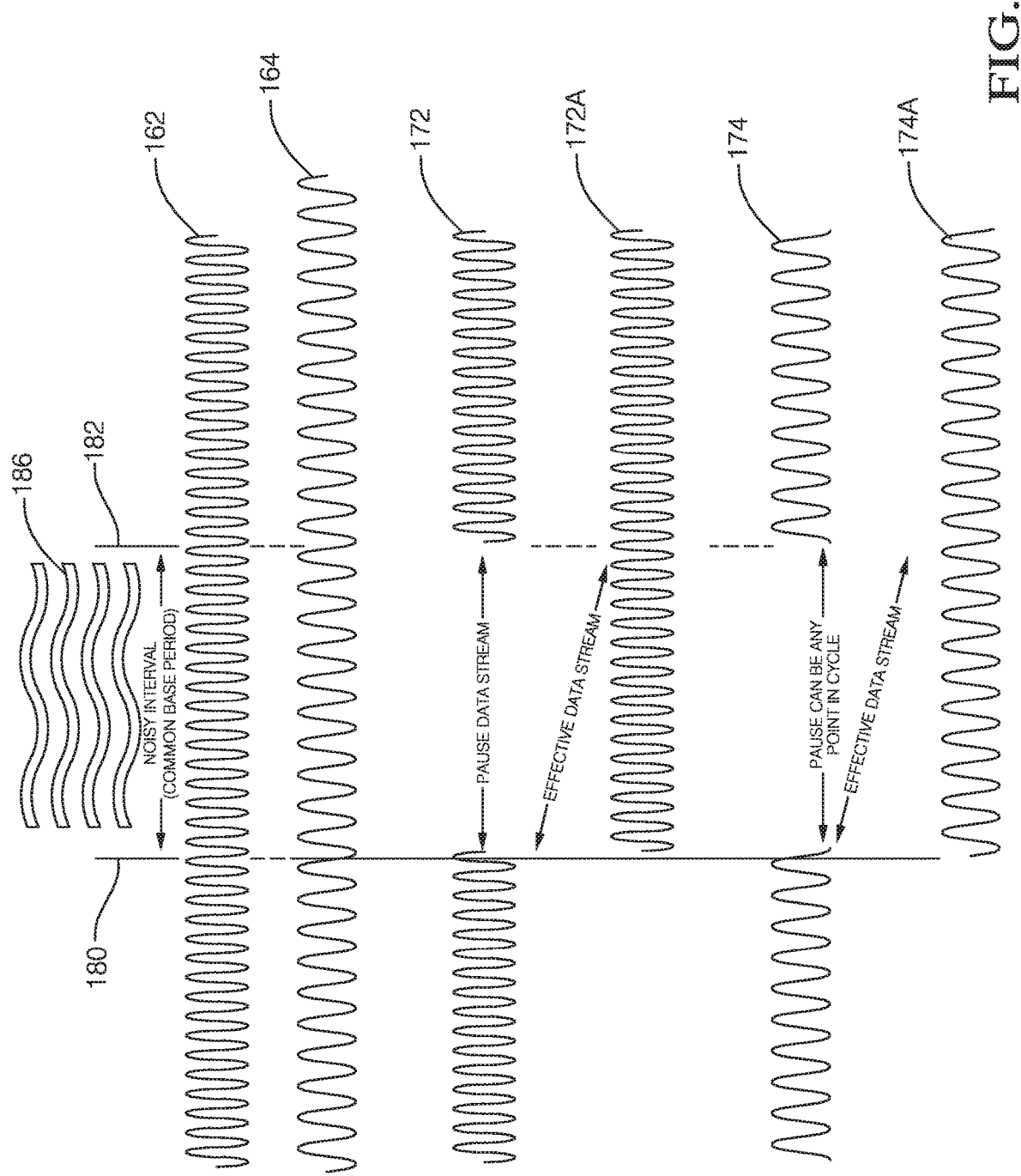
FIG. 8 illustrates pausing processing of response signals to allow for the operation of a noise generating device

The ability to resume processing of a multi-frequency response signal (e.g., demodulated data stream) at the same frequency point for all of the multiple frequencies allows for operating a noise generating device (e.g., magnetic field-based localization system) while processing of the response signal is paused. FIG. 8 illustrates pausing processing of response signals to allow for the operation of a noise generating device such as a magnetic field-based localization system. For simplicity, this example only illustrates two electrode drive signals (e.g., patch excitation signals), however, it will be appreciated that any number of drive signals are possible so long as the drive signals are orthogonal. As shown, the two drive signals 162, 164 have different frequencies while having a common base frequency (i.e., orthogonal signals). As shown, each of the drive signals 162, 164 is applied continuously. FIG. 8 also illustrates response signals (e.g., sensed signals) or demodulated data streams 172, 174 generated in response to application of the drive signals 162, 164, respectively. These data streams 172, 174 may represent the output of the demodulator(s) that will be received by the decimation filter(s). As shown, at a first point in time 180 (e.g., beginning of a base period), it may be desirable to, for example, obtain a magnetic field-based measurement of magnetic sensors or operate another noise generating device. Accordingly, the data streams 172, 174 for each of the sensed signals or demodulated data streams may be paused at the beginning of the base period 180 and resumed at the end of the base period 182 or integer multiple of the base period (e.g., 10 ms for a base frequency of 100 Hz). During this pause or skip, an electrical noise generating device such as a magnetic field generator may apply a signal 186 (e.g., magnetic field) after the beginning 180 of the base period and terminate the signal 186 a short time before the end of the base period. During the base period 184, the demodulated data streams are paused, and the data associated with these signals is discarded. At the end of the base period 182, the demodulated data streams resume entry into the filter at the exact frequency location in each sensed signal. Accordingly, the filter(s) sees an effective data stream 172A, 174A, from a frequency standpoint, that is continuous and without interruption. In effect, the pausing of the demodulated data streams into the filter(s) allows for interleaving the operation of a noise generating device such as a magnetic field-based localization system with a continuously operating impedance-based localization system without introducing noise into impedance-based measurements.

Figure 6C:
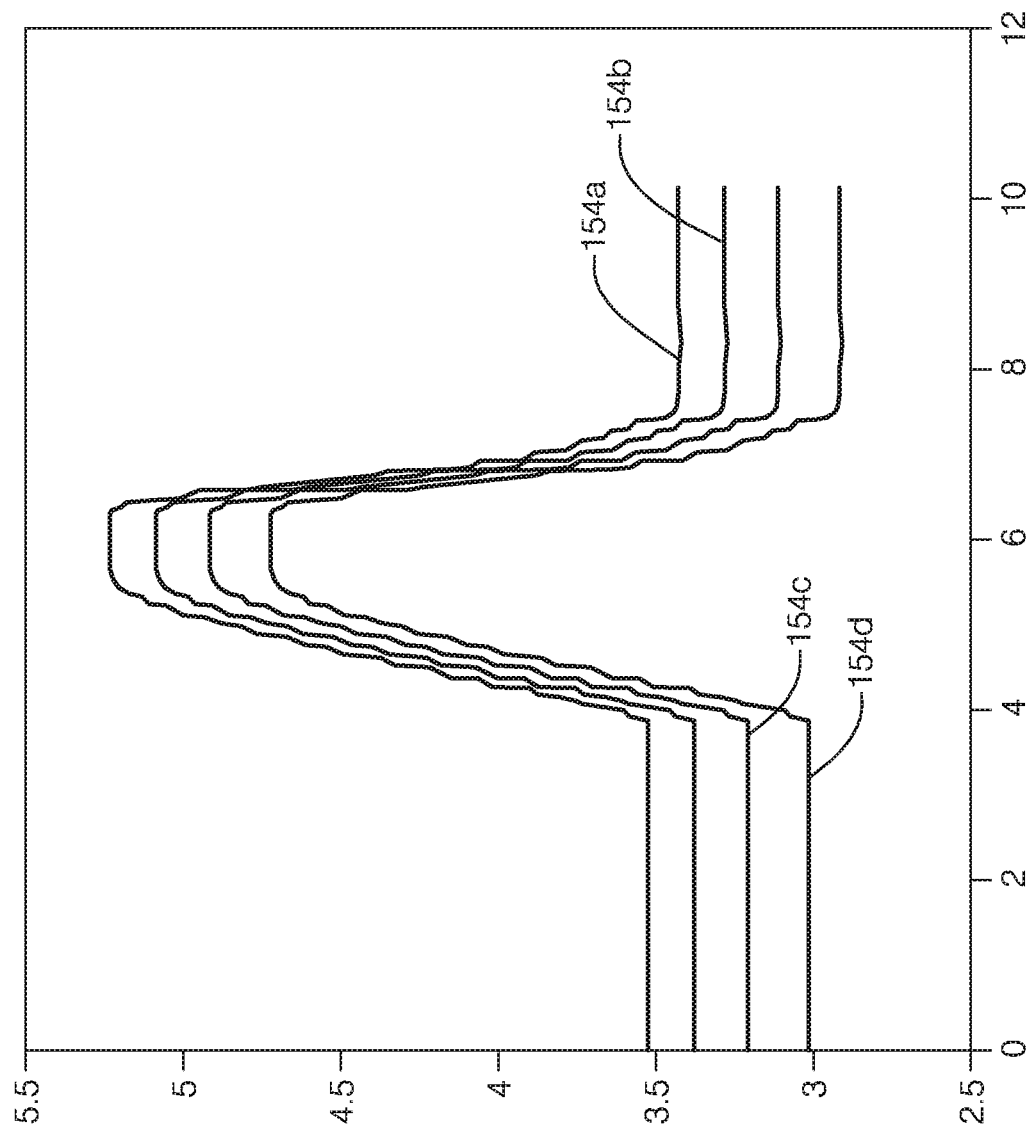

The pausing of the sensed signals allows the decimating filter to skip corrupted or noisy data. That is, the corrupted data is effectively discarded. This allows continued processing of the signals free of the noisy data. FIG. 6C illustrates a continuation of the graphically illustrated example of FIG. 6B where impedance location values for four electrodes are acquired during the operation of a magnetic field-based localization system. More specifically, FIG. 6C illustrates the location traces 154a-d that correspond to the location traces 152a-b of FIG. 6B. However, these location traces 154*a-d* are generated from data streams that are paused during the operation of the magnetic field-based localization system. That is, the decimating filter(s) skip the portions of the incoming data streams corresponding to the operation of the magnetic field-based localization system. As a result, the location traces 154*a-d* of FIG. 6C are significantly smoother (i.e., lower noise) than the location traces 152*a-d* of FIG. 6B and approaching the low noise level of location traces 150*a-d* generated free of any operation of a magnetic field-based localization system. See FIG. 6A.

Of note, the pausing of the demodulated data streams during a noise or interference event (e.g., operation of a magnetic field generator) requires precise time intervals to allow corrupt (e.g., noisy) impedance data to be held off from the decimating filter and properly resumed. As disclosed herein, the precise time intervals are measured in terms of discrete ADC samples. For example, 640 ADC samples corresponds to 10 ms when a sampling rate is 64 k/s. However, other means for precisely measuring the time intervals could be implemented though it is currently believed that ADC sample rate timing to be the most effective. Of further note, during a noise or interference event, while a data stream going into a decimation filter(s) is suspended, it is not necessary to suspend data (e.g., ADC output) from entering the demodulator(s) (e.g., synchronous multipliers 134) as the demodulator(s) has no memory beyond a current sample. That is, the demodulator only provides the most recent product for the digital response signal multiplied by the corresponding values of from the reference signals (e.g., drive signals).

Figure 9:
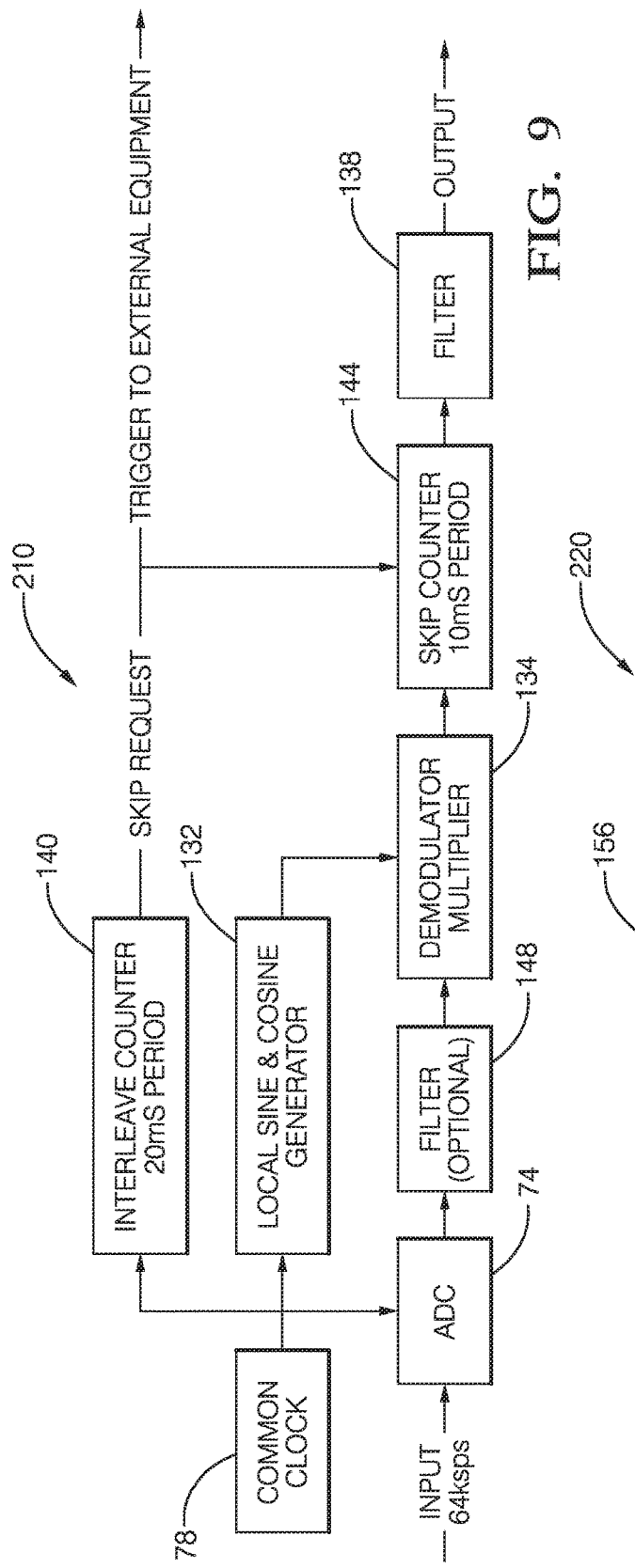
FIG. 9 illustrates one block diagram of one embodiment of a skip controller.

FIG. 9 illustrates one block diagram of one embodiment of a skip controller or skip control system 210 that may be implemented in the signal measuring circuit (e.g., signal sampler) and a synchronous demodulation circuit of FIG. 5 or in a similar circuit. The skip control system 210 permits interleaving response measurement of a continuously operating impedance-based localization system with another noise generating system or device such as a magnetic field-based localization system (e.g., external equipment). In this embodiment, the skip control system is used to interleave response measurements for a system using continuous orthogonal drive signals having a 10 ms base period. In the illustrated embodiment, a common clock 78 is connected to the ADC 74, the sine and cosine generator 132 (e.g., numerically controlled oscillator) and an interleave counter 140. The clock may utilize samples from the ADC 74 as a basis for timing. As illustrated, the ADC 74 receives an analog response signal from an electrode and converts the analog signal to a digital signal at a predetermined sampling rate (e.g., 64 k/s) that is provided to the demodulator multiplier 134. The demodulator multiplier demodulates the signal in accordance with the reference signal from the sine and cosine generator 132. Optionally, a buffer filter 148 may be provided between the output of the ADC and the input of the demodulator. Functionality this filter 148 is further discussed in relation to FIGS. 10 and 11.

The interleave counter 140 monitors the time from the common clock and/or ADC. In the present embodiment, at every 20 ms period (e.g., 1280 ADC samples for a sampling rate of 64 k/s), the interleave counter generates a skip request which is provided to trigger or initiate operation of an external equipment system such as a magnetic field-based localization system. The skip request is also provided to a skip counter 144 disposed between the demodulator/multiplier 134 and the decimating filter 138. In the present embodiment, the skip counter 144 begins counting a 10 ms period (e.g., 640 ADC samples for a sampling rate of 64 k/s), upon receiving the skip request. During this 10 ms period, the skip counter (or the controller) discards the incoming demodulated data stream from the demodulator multiplier 134 preventing entry of this potentially noisy data into the filter 138. During this 10 ms period, the external equipment may operate. For instance, the magnetic field-based localization system may energize magnetic coils to obtain magnetic measurements of one or more magnetic sensors. In such an arrangement, the external equipment is configured to start and complete its operation during the 10 ms skip period while the demodulated data stream is discarded. At the end of the 10 ms skip period, the demodulated data stream is provided to the filter 138 which processes the data stream (e.g., without frequency discontinuity) for the next 10 ms when the next skip request is received. In this embodiment, a 50/50 duty cycle or 1:1 interleave exists between the external equipment and the impedance-based system. However, it will be appreciated that other duty cycles are possible, for instance, the interleave counter period may be 30 ms providing 10 ms (one base period) the external equipment to operate and 20 ms (two base periods) for the impedance-based system to operate. Likewise, the skip counter 144 may have a 20 ms period providing the external equipment 20 ms to operate while the impedance-based system operates in the remaining 10 ms. Any combination is possible as long at the interleave counter and skip counter utilize integer multiples of the base period of the impedance drive signals associated with the incoming response signal.

Though primarily discussed above as allowing the interleaving of impedance-based measurements with magnetic field-based measurements, it will be appreciated that the interleaving process may be applied to other noise generating systems. For example, with minor changes, cardiac pacing pulses may also be rejected from the impedance processing system, minimizing the otherwise large disturbance caused by a pacing pulse. During cardiac procedures, it is common to use an external pacing system to stimulate the heart as part of diagnosis. The pacing pulse is generally at the rate of desired beats per minute, for example, 60 to 120 bpm. The pulse is of a short duration, usually under 10 milliseconds, but of a very large electrical amplitude. This short pulse disturbs the measured impedance responses for a very short time. The present disclosure may be modified to providing a "blanking" function that effectively removes the pacing pulse. That is, detecting the pacing pulse and keeping it out of the signal processing of the decimating filter, as described above, effectively suppresses the pacing pulse from the impedance data. Further, such a blanking function may be utilized to detect and suppress any anomalous event that results in a spike in a received response signal.

Figure 10:
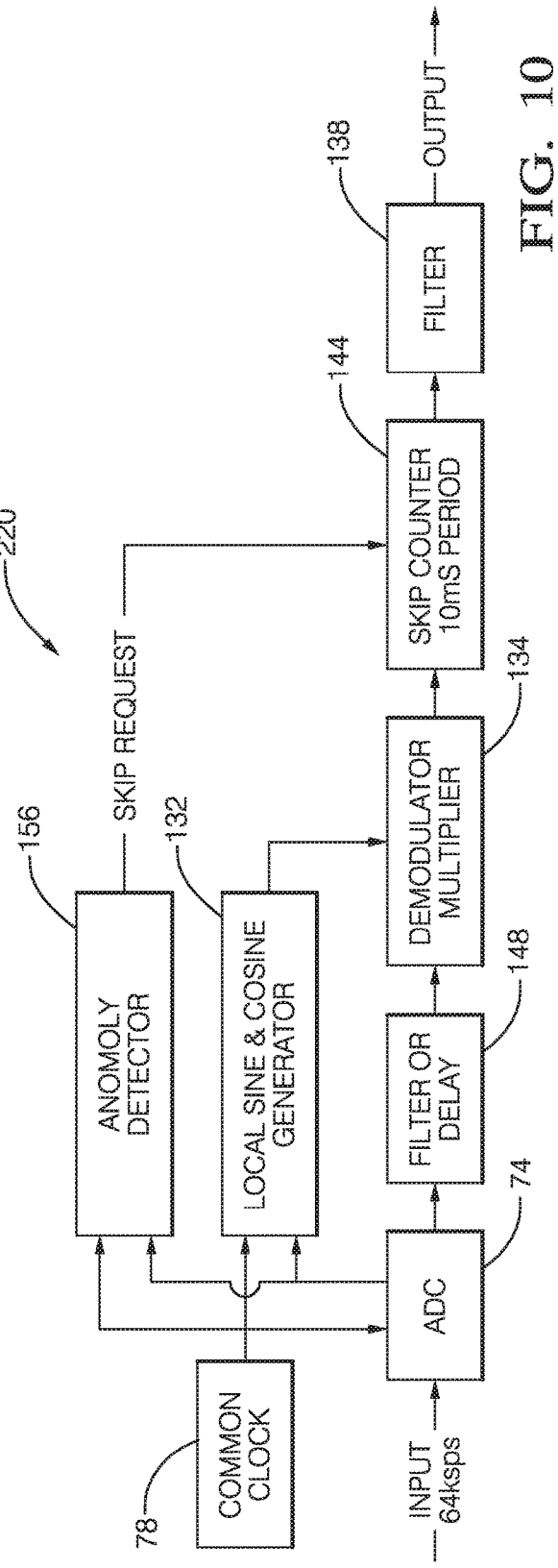
FIG. 10 illustrates one block diagram of one embodiment of a blanking controller.

FIG. 10 illustrates one block diagram of one embodiment of a blanking controller or blanking control system 220. As illustrated, the blanking control system 220 shares a number of common components with the skip control system 210 of FIG. 9. Accordingly, like components utilize like reference numbers. As shown, the blanking control system incorporates an anomaly detector 156 connected to the output of the ADC 74. The detection of an anomaly, such as a pacing pulse, is performed by measuring the sample-to-sample difference (slew rate) of the output of the ADC 74. That is, adjacent samples of the ADC are compared and if a difference between the samples is greater than a predetermined threshold, the anomaly detector outputs a skip request to the skip counter 144. The skip counter 144 begins counting a 10 ms period (e.g., one base period in the present example) upon receiving the skip request. During this 10 ms period, the skip counter discards the incoming demodulated data stream from the demodulator/multiplier 134 preventing entry of this potentially noisy data into the filter 138 and thereby blanking the anomalous event (e.g., presuming the anomalous event is shorter that 10 ms in duration).

In order to blank unknown anomalous events as they arrive in the measurement circuit, a buffer or delay filter 148 is disposed between the ADC 74 and the demodulator multiplier 134. The delay filer 148 briefly stores a small set of ADC samples (e.g., in memory) to temporarily store data to allow the detector 156 time to analyze the samples and, when necessary, output a skip request. Only a small number of ADC samples are required, on the order of 10 to 20. A small storage buffer of this many samples is used such that the samples are delayed by a corresponding number of sample periods. At a sampling rate 64 k/s, this is a delay of only 156 to 312 microseconds, an imperceptible delay to a user. This short delay prevents the samples corrupted by the anomalous event (e.g., pacing pulse) reaching the decimation filter 138 before skipping (processing suspension) begins. If the anomalous event continues beyond 10 ms (e.g., one base period in the present example), the anomaly detector 156 may issue another one base period skip request. However, this is not a requirement. In any embodiment, the blanking control system 220 allows for removing unforeseen noise form the signals before they are processed.

Figure 11:
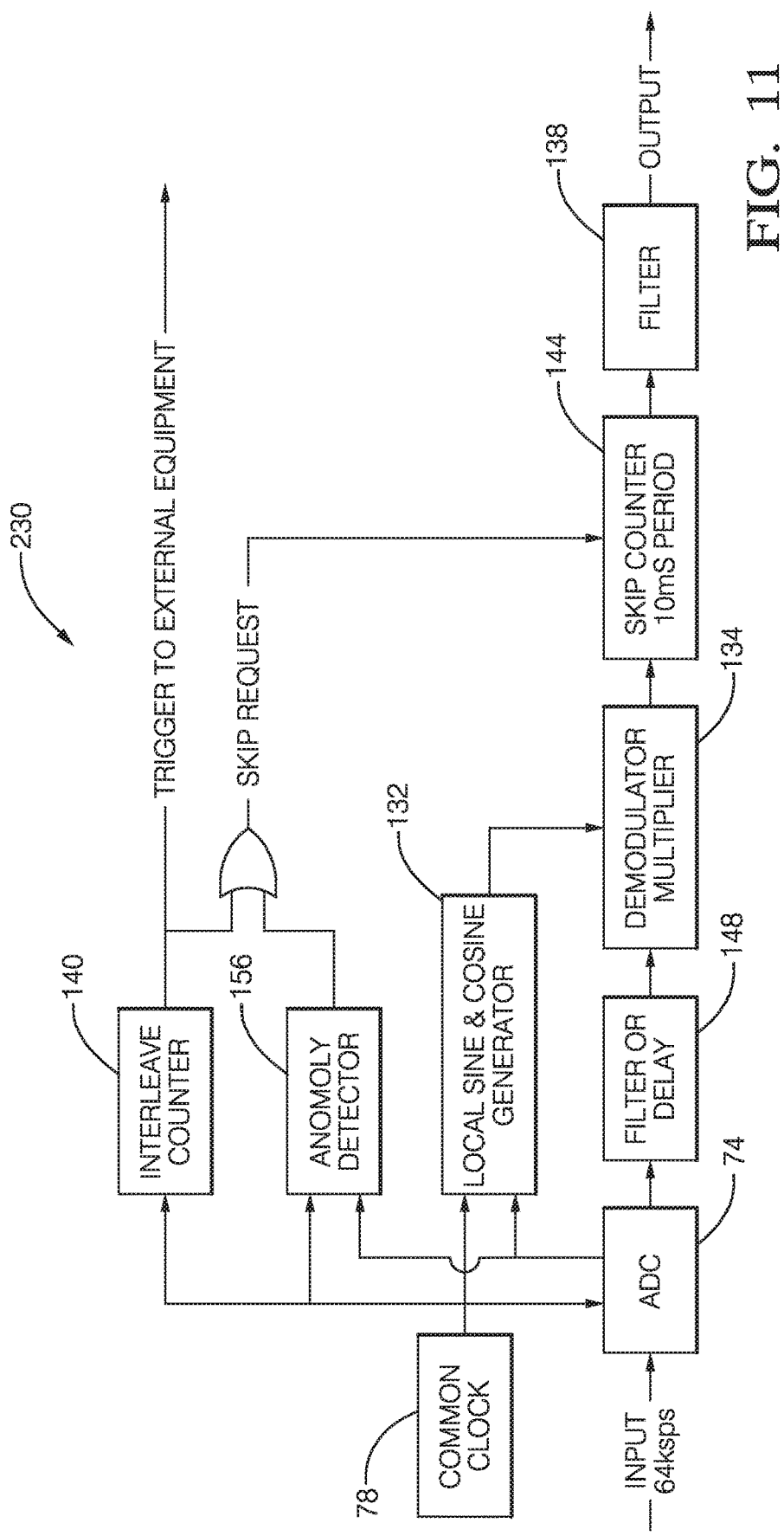
FIG. 11 illustrates one block diagram of one embodiment of a combined skip controller and blanking controller.

FIG. 11 illustrates a combined control system 230 that combines the functionality of the skip control system 210 and the blanking control system 220. As illustrated, the combined control system 230 is operative to utilize the interleave counter 140 to issue skip request and trigger external equipment. In addition, the Anomaly detector 156 may issue skip request upon identifying an incoming anomalous event, such as a pacing pulse.

Figure 12:
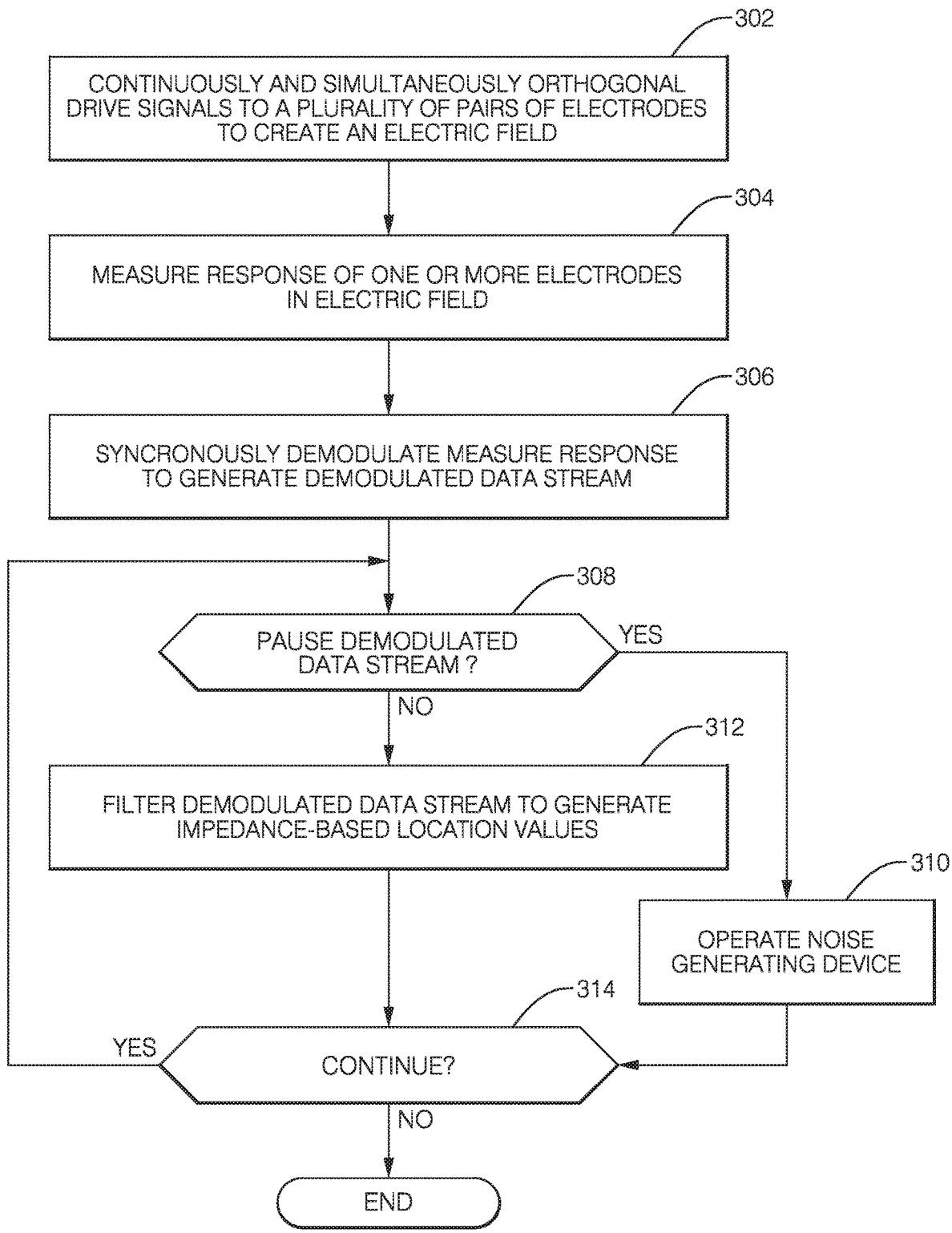
FIG. 12 illustrates one process diagram for interleaving a noise generating device with impedance measurements.

FIG. 12 illustrates a process flow sheet illustrating one process 300 for interleaving impedance measurements with the operation of a noise generating device such as a magnetic field-based localization system. Initially, orthogonal drive signals are continuously and simultaneously applied 302 to patch electrodes of an impedance-based localization system to create an electric field. Once the electric field is generated, a response of an electrode (e.g., catheter electrode within the electric field) to all of the drive signals is measured 304. Such measurement typically includes converting the measured response to a digital signal as discussed above. A demodulator synchronously demodulates 306 the measured response to generate a demodulated data stream 306. Once demodulated, a decision may be made regarding if the demodulated data stream should be input into a filter (decimating filter). That is, a decision to pause 308 the data stream is made. Such a pause decision may be based on a duty cycle (e.g., timer, ADC cycles etc.) for operating the impedance-based localization system and an external noise generating device (e.g., magnetic field-based localization system), if the data stream is paused, a noise generating device may operate 310 for a time period that is an integer multiple of a base period of the orthogonal drive signals. If the data stream is not paused, the data stream enters the filter, which down-samples/filters 312 the data stream to generate impedance-based location value. If the process 300 continues 314, the filter continues filtering 312 data stream continues being processed by the filter until the next pause decision.

All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A position sensing and navigation system for use in navigating a medical device within a body of a patient, comprising:
   an impedance-based localization system having:
      a signal generator to apply each one of a plurality of drive signals across a corresponding one of a plurality of pairs of patch electrodes to create an electric field, wherein the drive signals each have a unique frequency that is a harmonic of a common base frequency;
      a demodulator configured to synchronously demodulate a composite response signal of at least one electrode of a medical device, disposed in the electric field, to the plurality of drive signals and output a demodulated data stream; and
      a filter configured to receive the demodulated data stream and output impedance-based values proportional to the location of the at least one electrode for each unique frequency,
      wherein the signal generator applies the plurality of drive signals continuously and simultaneously across the plurality of patch electrodes to create the electric field;
   a magnetic field-based localization system having:
      a magnetic field generator for generating a magnetic field for use in acquiring a magnetic response from at least one magnetic sensor of the medical device disposed in the magnetic field; and
      a controller configured to pause input of the demodulated data stream into the filter during operation of the magnetic field generator.

2. The system of claim 1, further comprising:
a model construction system configured to utilize the impedance-based values to generate a model of the medical device; and
a display configured to display an image of the model of the medical device.

3. The system of claim 1, wherein the controller is configured to pause the input of the demodulated data stream into the filter for a time period that is an integer multiple of a base period of the common base frequency.

4. The system of claim 3, further comprising:
an analog to digital converter (ADC) configured to convert the composite response signal to a digital response signal prior to entry of the composite response signal into the demodulator, wherein the time period is measured in terms of discrete ADC samples.

5. The system of claim 3, wherein the controller discards the demodulated data stream during the time period.

6. The system of claim 3, wherein the controller is configured to initiate operation of the magnetic field-based localization system during the time period.

7. The system of claim 3, wherein the controller is configured to:
initiate operation of the magnetic-field based localization system during a first time period where the demodulated data stream into the filter is paused; and
permit the demodulated data stream into the filter during a separate second time period, wherein the first and second time periods are each integer multiples of the base period of the common base frequency.

8. The system of claim 7, wherein the first time period and the second time period are different.

9. The system of claim 1, further comprising:
a detector configured to analyze digital samples of the composite response signal prior to entry of the digital samples into the demodulator; and
a buffer configured to store a predetermined set of the digital samples prior to entry of the digital samples into the demodulator, wherein the detector is configured to:
compare a slew rate of the digital sample to a predetermined threshold; and
pause input of the demodulated data stream into the filter if the slew rate exceeds the predetermined threshold.

10. An electronic control unit for use in navigating a medical device within a body of a patient, comprising:
a signal generator configured to generate a plurality of drive signals each having a unique frequency that is a harmonic of a common base frequency, wherein the plurality of drive signals are simultaneously and continuously applicable across a corresponding plurality of individual pairs of patch electrodes to create an electric field;
a demodulator configured to synchronously demodulate a composite response signal of at least one electrode of a medical device disposed in the electric field for the plurality of drive signals and output a demodulated data stream;
a filter configured to receive the demodulated data stream and output impedance-based values proportional to the location of the at least one electrode for each unique frequency; and
a controller configured to:
pause input of the demodulated data stream into the filter; and
initiate operation of a device that generates electrical noise while the demodulated data stream into the filter is paused.

11. The system of claim 10, further comprising:
a model construction system configured to utilize the impedance-based values to generate a model of the medical device; and
a display configured to display an image of the model of the medical device.

12. The system of claim 10, wherein the controller is configured to pause the input of the demodulated data stream into the filter for a time period that is an integer multiple of a base period of the common base frequency.

13. The system of claim 10, wherein the controller discards the demodulated data stream during the time period.

14. The system of claim 10, wherein the device that generates electrical noise comprises a magnetic field-based localization system.

15. The system of claim 10, further comprising:
a detector configured to analyze digital samples of the composite response signal prior to entry of the digital samples into the demodulator; and
a buffer configured to store a predetermined set of the digital samples prior to entry of the digital samples into the demodulator, wherein the detector is configured to:
compare a slew rate of the digital sample to a predetermined threshold; and
pause input of the demodulated data stream into the filter if the slew rate exceeds the predetermined threshold.

16. A method for use in sensing the position of an elongated medical device within a body of a patient, comprising:
generating a plurality of drive signals each having a unique frequency that is a harmonic of a common base frequency and simultaneously applying each of the plurality of drive signals across a corresponding one of a plurality of pairs of patch electrodes to generate an electric field;
measuring a composite response signal of at least one electrode of a medical device disposed in the electric field to the plurality of drive signals;
synchronously demodulating the composite response signal of the at least one electrode to output a demodulated data stream; and
pausing the demodulated data stream during an electric noise generating event where the demodulated data stream is discarded for a time period, wherein the time period is an integer multiple of a base period of the common base frequency;
filtering the demodulated data stream to output impedance-based values proportional to the location of the at least one electrode for each unique frequency;
utilizing the impedance-based values to generate a model of the medical device; and
displaying an image of the model of the medical device.

17. The method of claim 16, wherein pausing the demodulated data stream is performed on a predetermined duty cycle.

18. The method of claim 16, wherein pausing the demodulated data stream during an electric noise generating event further comprises:
pausing the demodulated data stream;
initiating operation of an electric noise garneting device;
deactivating operation of the noise generating device prior to the end of the time period; and
resuming the filtering of the demodulated data.

19. The method of claim 16, wherein pausing the demodulated data stream is performed in response to identification of an anomalous event.

20. The method of claim 19, further comprising:
comparing samples of the composite response signal prior to the demodulating; and
identifying a difference between samples that is greater than a predetermined threshold; and
initiation the pausing of the demodulated data stream for the time period.

* * * * *

UNITED STATES PATENT AND TRADEMARK OFFICE
CERTIFICATE OF CORRECTION

PATENT NO. : 12,137,988 B2
APPLICATION NO. : 17/619990
DATED : November 12, 2024
INVENTOR(S) : Timothy G. Curran Page 1 of 1

It is certified that error appears in the above-identified patent and that said Letters Patent is hereby corrected as shown below:

In the Claims

Column 20, Line 64, Claim 18, "initiating operation of an electric noise garneting device;" should read
-- initiating operation of an electric noise generating device; --

Signed and Sealed this
Twenty-second Day of April, 2025

Coke Morgan Stewart
*Acting Director of the United States Patent and Trademark Office*